(12) United States Patent
Hughes et al.

(10) Patent No.: US 9,326,949 B2
(45) Date of Patent: May 3, 2016

(54) METHOD OF MAKING OIL-IN-OIL EMULSIFIED POLYMERIC IMPLANTS CONTAINING A HYPOTENSIVE LIPID

(71) Applicant: Allergan, Inc., Irvine, CA (US)

(72) Inventors: Patrick M. Hughes, Aliso Viejo, CA (US); Michele Boix, Cantaron (FR); Christian Sarrazin, Pegomas (FR); Marina Do, Menton (FR)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/679,396

(22) Filed: Apr. 6, 2015

(65) Prior Publication Data

US 2015/0272898 A1  Oct. 1, 2015

Related U.S. Application Data

(60) Division of application No. 13/861,688, filed on Apr. 12, 2013, now Pat. No. 8,999,397, which is a continuation of application No. 13/152,780, filed on Jun. 3, 2011, now Pat. No. 8,445,027, which is a (Continued)

(51) Int. Cl.
 *B01J 13/02* (2006.01)
 *A61K 9/50* (2006.01)
 (Continued)

(52) U.S. Cl.
 CPC ............ *A61K 9/5089* (2013.01); *A61K 9/0048* (2013.01); *A61K 9/0051* (2013.01); *A61K 9/1075* (2013.01); *A61K 9/1647* (2013.01); *A61K 9/1694* (2013.01);

(Continued)

(58) Field of Classification Search
 CPC .. A61K 9/1647; A61K 9/1694; A61K 9/1075
 See application file for complete search history.

(56) References Cited

U.S. PATENT DOCUMENTS 3,396,081 A   8/1968 Billek et al.
3,749,776 A   7/1973 Eakins et al.
(Continued)

FOREIGN PATENT DOCUMENTS

CA   1333770   1/1995
EP   0251680   1/1988
(Continued)

OTHER PUBLICATIONS

Allergan, Alphagan Product Information, Product Sheet, 2005, 1-10.
(Continued)

*Primary Examiner* — Carlos Azpuru
(74) *Attorney, Agent, or Firm* — Laura L. Wine; Joel B. German; Debra D. Condino

(57) ABSTRACT

Biocompatible intraocular implants, such as microparticles, include a prostamide component and a biodegradable polymer that is effective in facilitating release of the prostamide component into an eye for an extended period of time. The prostamide component may be associated with a biodegradable polymer matrix, such as a matrix of a two biodegradable polymers. Or, the prostamide component may be encapsulated by the polymeric component. The present implants include oil-in-oil emulsified implants or microparticles. Methods of producing the present implants are also described. The implants may be placed in an eye to treat or reduce a at least one symptom of an ocular condition, such as glaucoma.

12 Claims, 9 Drawing Sheets

Related U.S. Application Data division of application No. 11/303,462, filed on Dec. 15, 2005, now Pat. No. 7,993,634, which is a continuation-in-part of application No. 10/837,260, filed on Apr. 30, 2004, now Pat. No. 7,799,336.

(51) Int. Cl.

| | | |
|---|---|---|
| *A61K 9/16* | (2006.01) | |
| *A61K 9/107* | (2006.01) | |
| *A61K 9/00* | (2006.01) | |
| *A61K 47/34* | (2006.01) | |
| *B01J 13/04* | (2006.01) | |
| *B01J 13/06* | (2006.01) | |
| *A61K 31/165* | (2006.01) | |
| *A61K 31/216* | (2006.01) | |
| *A61K 31/5575* | (2006.01) | |

(52) U.S. Cl.
CPC ............ *A61K 9/5031* (2013.01); *A61K 31/165* (2013.01); *A61K 31/216* (2013.01); *A61K 31/5575* (2013.01); *A61K 47/34* (2013.01); *B01J 13/02* (2013.01); *B01J 13/04* (2013.01); *B01J 13/06* (2013.01)

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,396,625 A | 8/1983 | Yamamori et al. |
| 4,425,346 A | 1/1984 | Horlington et al. |
| 4,454,151 A | 6/1984 | Waterbury |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,932,984 A | 6/1990 | Nankee et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,028,624 A | 7/1991 | Chan et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,166,331 A | 11/1992 | Della Valle |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith |
| 5,384,333 A | 1/1995 | Davis et al. |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,501,856 A | 3/1996 | Ohtori et al. |
| 5,504,074 A | 4/1996 | D'Amato et al. |
| 5,516,522 A | 5/1996 | Peyman et al. |
| 5,523,301 A | 6/1996 | Amon et al. |
| 5,585,401 A | 12/1996 | Brandt et al. |
| 5,587,371 A | 12/1996 | Sessler et al. |
| 5,587,479 A | 12/1996 | Makovec et al. |
| 5,597,897 A | 1/1997 | Ron et al. |
| 5,612,364 A | 3/1997 | York et al. |
| 5,655,832 A | 8/1997 | Pelka et al. |
| 5,656,297 A | 8/1997 | Berstein et al. |
| 5,688,819 A | 11/1997 | Woodward et al. |
| 5,707,643 A | 1/1998 | Ogura |
| 5,716,981 A | 2/1998 | Hunter et al. |
| 5,766,242 A | 6/1998 | Wong et al. |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 5,965,152 A | 10/1999 | Galin et al. |
| 5,972,326 A | 10/1999 | Galin et al. |
| 6,051,576 A | 4/2000 | Ashton et al. |
| 6,066,675 A | 5/2000 | Wen et al. |
| 6,074,661 A | 6/2000 | Olejnik et al. |
| 6,217,869 B1 | 4/2001 | Meyer et al. |
| 6,217,895 B1 | 4/2001 | Guo et al. |
| 6,225,303 B1 | 5/2001 | Miller et al. |
| 6,258,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,309,669 B1 | 10/2001 | Setterstrom et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,395,787 B1 | 5/2002 | Woodward et al. |
| 6,403,649 B1 | 6/2002 | Woodward |
| 6,455,062 B1 | 9/2002 | Olejnik et al. |
| 6,482,854 B1 | 11/2002 | Lipton et al. |
| 6,497,729 B1 | 12/2002 | Moussy et al. |

(56) References Cited

U.S. PATENT DOCUMENTS

| | | | |
|---|---|---|---|
| 6,537,568 B2 | 3/2003 | Olejnik et al. | |
| 6,548,078 B2 | 4/2003 | Guo et al. | |
| 6,565,871 B2 | 5/2003 | Roser et al. | |
| 6,573,280 B2 | 6/2003 | Dreyer | |
| 6,595,945 B2 | 7/2003 | Brown | |
| 6,699,493 B2 | 3/2004 | Wong | |
| 6,713,081 B2 | 3/2004 | Robinson et al. | |
| 6,726,918 B1 | 4/2004 | Wong et al. | |
| 6,765,012 B2 | 7/2004 | Andrews et al. | |
| 6,899,717 B2 | 5/2005 | Lathrop et al. | |
| 7,091,231 B2 | 8/2006 | Donde | |
| 7,476,747 B2 | 1/2009 | Old | |
| 7,589,057 B2 | 9/2009 | Chang et al. | |
| 7,592,364 B2 | 9/2009 | Old et al. | |
| 7,771,742 B2 | 8/2010 | Hughes et al. | |
| 7,799,336 B2 | 9/2010 | Hughes et al. | |
| 7,820,661 B2 | 10/2010 | Old et al. | |
| 7,993,634 B2 | 8/2011 | Hughes et al. | |
| 8,119,154 B2 | 2/2012 | Huang et al. | |
| 8,147,865 B2 | 4/2012 | Huang et al. | |
| 8,206,736 B2 | 6/2012 | Hughes | |
| 8,206,737 B2 | 6/2012 | Hughes | |
| 8,293,210 B2 | 10/2012 | Huang et al. | |
| 8,445,027 B2 | 5/2013 | Hughes | |
| 8,722,097 B2 | 5/2014 | Chang et al. | |
| 8,911,767 B2 | 12/2014 | Hughes | |
| 8,969,415 B2 | 3/2015 | Robinson et al. | |
| 8,999,397 B2 * | 4/2015 | Hughes et al. | 424/502 |
| 9,006,464 B2 | 4/2015 | Donde et al. | |
| 2001/0023363 A1 | 9/2001 | Harth et al. | |
| 2002/0032201 A1 | 3/2002 | Olejnik | |
| 2002/0035264 A1 | 3/2002 | Kararli | |
| 2002/0040015 A1 | 4/2002 | Miller et al. | |
| 2002/0094998 A1 | 7/2002 | Burke et al. | |
| 2002/0103255 A1 | 8/2002 | Hellberg et al. | |
| 2003/0018078 A1 | 1/2003 | Woodward et al. | |
| 2003/0069286 A1 | 4/2003 | Chen et al. | |
| 2003/0069560 A1 | 4/2003 | Adamis et al. | |
| 2003/0095995 A1 | 5/2003 | Wong et al. | |
| 2003/0185873 A1 | 10/2003 | Chasin et al. | |
| 2003/0199478 A1 | 10/2003 | Andrews et al. | |
| 2003/0220376 A1 | 11/2003 | Masferrer | |
| 2003/0225152 A1 | 12/2003 | Andrews et al. | |
| 2004/0054374 A1 | 3/2004 | Weber et al. | |
| 2004/0058313 A1 | 3/2004 | Abreu | |
| 2004/0127843 A1 | 7/2004 | Tu | |
| 2004/0137059 A1 | 7/2004 | Nivaggioli | |
| 2004/0151753 A1 | 8/2004 | Chen et al. | |
| 2004/0208910 A1 | 10/2004 | Ashton et al. | |
| 2004/0234611 A1 | 11/2004 | Ahlheim et al. | |
| 2005/0003007 A1 | 1/2005 | Boix et al. | |
| 2005/0107463 A1 | 5/2005 | Woodward | |
| 2005/0112175 A1 | 5/2005 | Yaacobi | |
| 2005/0113806 A1 | 5/2005 | DeCarvalho | |
| 2005/0175708 A1 | 8/2005 | Carrasquillo et al. | |
| 2005/0192264 A1 | 9/2005 | Penfold | |
| 2005/0244458 A1 | 11/2005 | Huang et al. | |
| 2005/0244461 A1 | 11/2005 | Nivaggioli et al. | |
| 2005/0244462 A1 | 11/2005 | Farooq | |
| 2005/0244463 A1 | 11/2005 | Huang | |
| 2005/0244464 A1 | 11/2005 | Hughes | |
| 2005/0244465 A1 | 11/2005 | Nivaggioli et al. | |
| 2005/0244466 A1 | 11/2005 | Whitcup et al. | |
| 2005/0244467 A1 | 11/2005 | Nivaggioli et al. | |
| 2005/0244468 A1 | 11/2005 | Huang et al. | |
| 2005/0244469 A1 | 11/2005 | Whitcup et al. | |
| 2005/0244470 A1 | 11/2005 | Hughes et al. | |
| 2005/0244471 A1 | 11/2005 | Shiah et al. | |
| 2005/0244477 A1 | 11/2005 | Hughes et al. | |
| 2005/0244478 A1 | 11/2005 | Hughes et al. | |
| 2005/0244479 A1 | 11/2005 | Huang et al. | |
| 2005/0244506 A1 | 11/2005 | Burke et al. | |
| 2005/0271705 A1 | 12/2005 | Hughes | |
| 2006/0013859 A1 | 1/2006 | Yamada et al. | |
| 2006/0173060 A1 | 8/2006 | Chang et al. | |
| 2006/0182781 A1 | 8/2006 | Hughes | |
| 2006/0210604 A1 | 9/2006 | Dadey | |
| 2006/0246145 A1 | 11/2006 | Chang | |
| 2007/0129552 A1 | 6/2007 | Donde | |
| 2007/0142376 A1 | 6/2007 | Fleenor et al. | |
| 2007/0203222 A1 | 8/2007 | Old | |
| 2007/0224246 A1 | 9/2007 | Hughes et al. | |
| 2007/0233037 A1 | 10/2007 | Gifford et al. | |
| 2007/0265330 A1 | 11/2007 | Old | |
| 2008/0033351 A1 | 2/2008 | Trogden | |
| 2008/0131481 A1 | 6/2008 | Hughes | |
| 2008/0131482 A1 | 6/2008 | Hughes | |
| 2008/0131484 A1 | 6/2008 | Robinson | |
| 2008/0145403 A1 | 6/2008 | Spada | |
| 2008/0269498 A1 | 10/2008 | Old | |
| 2008/0292679 A1 | 11/2008 | Lyons | |
| 2008/0312321 A1 | 12/2008 | Donde et al. | |
| 2009/0082863 A1 | 3/2009 | Schieber | |
| 2009/0124676 A1 | 5/2009 | Donde et al. | |
| 2010/0074957 A1 | 3/2010 | Robinson et al. | |
| 2010/0098772 A1 | 4/2010 | Robinson et al. | |
| 2010/0104654 A1 | 4/2010 | Robinson et al. | |
| 2010/0124565 A1 | 5/2010 | Spada et al. | |
| 2010/0210689 A1 | 8/2010 | Old et al. | |
| 2010/0247606 A1 | 9/2010 | Robinson | |
| 2010/0278898 A1 | 11/2010 | Hughes et al. | |
| 2010/0310637 A1 | 12/2010 | Abdulrazik et al. | |
| 2011/0028523 A1 | 2/2011 | Nguyen et al. | |
| 2011/0160210 A1 | 6/2011 | Fleenor et al. | |
| 2011/0182966 A1 | 7/2011 | Robinson | |
| 2011/0250285 A1 | 10/2011 | Hughes | |
| 2012/0219611 A1 | 8/2012 | Hughes | |
| 2012/0238633 A1 | 9/2012 | Hughes | |
| 2013/0071349 A1 | 3/2013 | Robinson et al. | |
| 2014/0235681 A1 | 8/2014 | Whitcup et al. | |

FOREIGN PATENT DOCUMENTS

| | | |
|---|---|---|
| EP | 0364417 | 9/1989 |
| EP | 0490305 | 6/1992 |
| EP | 0322319 | 8/1992 |
| EP | 0430539 | 10/1994 |
| EP | 1541151 | 6/2005 |
| WO | 94-14417 | 7/1994 |
| WO | 95-13765 | 5/1995 |
| WO | 95-15748 | 6/1995 |
| WO | 95-35097 | 12/1995 |
| WO | 96-38174 | 12/1996 |
| WO | 97-26869 | 7/1997 |
| WO | 99-05263 | 2/1999 |
| WO | 00-04898 | 2/2000 |
| WO | 00-04899 | 3/2000 |
| WO | 00-37056 | 6/2000 |
| WO | 01-30323 | 5/2001 |
| WO | 01-58240 | 8/2001 |
| WO | 02-02076 | 1/2002 |
| WO | 02-05815 | 1/2002 |
| WO | 02-09787 | 2/2002 |
| WO | 02-43785 | 6/2002 |
| WO | 02-085248 | 10/2002 |
| WO | 03-013477 | 2/2003 |
| WO | 03-020172 | 3/2003 |
| WO | 03-024420 | 3/2003 |
| WO | 03-047513 | 6/2003 |
| WO | 03-047513 A2 | 6/2003 |
| WO | 03-074038 | 9/2003 |
| WO | 03-103772 | 12/2003 |
| WO | 2004-014352 | 2/2004 |
| WO | 2004-019938 | 3/2004 |
| WO | 2009-098458 | 8/2009 |
| WO | 2009-143288 A1 | 11/2009 |
| WO | 2010-093945 | 8/2010 |

OTHER PUBLICATIONS

Allergan, Inc., Tazorac Product Information Sheet, 2004, 1-8.

AlphaganP, Physician's Desk Reference, Product Information, 54th Edition, 493-494, 2001.

(56) References Cited

OTHER PUBLICATIONS

Anderson, Lynne et al, An Injectable Sustained Release Fertility Control System, Contraception, 1976, 375-384, 13.

Andreas, Kristin et al, Biodegradable insulin-loaded PLGA microspheres fabricated by three different emulsification techniques: investigation for cartilage tissue engineering, Acta Biomaterialia, 2011, 1485-1495, 7.

Arshady, Reza, Preparation of biodegradable microspheres and microcapsules: 2. Polyactides and related polyesters, J. Controlled Release, 1991, 1-22, 17.

Baker, Richard, Controlled Release of Biologically Active Agent, A Wiley, 1987, 73-75, Interscience Publication.

Bito, Laszlo, A new approach to the medical management of glaucoma, from the bench to the clinic, and beyond, Investigative Ophthalmology & Visual Science, 2001, 1126-1133, 42(6), The Proctor Lecture.

Bito, LZ, Biological Protection with Prostanoids, CRC Press, Inc., 1985, 231-252, 1, Cohen, M. M., ed., Boca Raton, Fla.

Bito, LZ, Prostaglandins, Old Concepts and New Perspectives, Archives of Ophthalmology, 1987, 1036-1039, 105.

Bito, LZ, Prostaglandins, Other Eicosanoids, and Their derivatives as Potential Antiglaucoma Agents, Glaucoma: Applied Pharmacology, 1984, 477-505, 20.

Bodor, Nicholas et al, A Comparison of Intraocular Pressure Elevating Activity of Loteprednoletabonate and Dexamethasone in Rabbits, Current Eye Research, 1992, 525-530, 11.

Brubaker, Richard, Mechanism of Action of Bimatoprost (LumiganTM), Surv Ophthalmol, 2001, S347-S351, 45—Suppl 4.

Busse, Dagmar et al, Tyrosine Kinase Inhibitors: Rationale, Mechanisms of Action, and Implications for Drug Resistance, Semin Oncol, 2001, 47-55, 28—Suppl 16.

Camras, C.B., Reduction of Intraocular Pressure by Prostaglandins Applied topically to the Eyes of Conscious Rabbits, Investigative Ophthalmology & Visual Science, Dec. 1977, 1125-1134, 16(12), US.

Cantor, LB, An Update on Bimatoprost in Glaucoma Therapy, Expert Opin Pharmacother, Dec. 2002, 1753-1762, 3 (12).

Casser, Linda et al, Subconjunctival Injection, Atlas of Primary Eyecare Procedures, 1997, 432-435, 2.

Cen, Jie et al, Preliminary evaluation of biodegradable implant for intraocular sustained-release of cefuroxime in rabbits, Journal of Shanghai Jiaotong, Jun. 2008, 644-647, 28(6).

Charles, Jean-Bernard et al, Use of Bioerodible Polymers Impregnated with Mitomycin in Glaucoma Filtration Surgery in Rabbits, Ophthalmology, Apr. 1991, 503-508, 98-4.

Chen, June et al, LumiganR: A Novel Drug for Glaucoma Therapy, Optom in Pract., Jun. 12, 2002, 95-102, 3.

Cheng, Cheng-Kuo et al., Intravitreal Sustained-Release Dexamethasone Device in the Treatment of Experimental Uveites, Investigative Ophthalmology & Visual Science, 1995, 442-453, 96 (2), US.

Chiang, Chiao-Hsi et al, Pharmacokinetics and Intraocular Pressure Lowering Effect of Timolol Preparations in Rabbit Eyes, Journal of Ocular Pharmacology and Therapeutics, 1996, 471-480, 12(4).

Clive, Migdal, Lumigan(R): A New Ocular Hypotensive Agent for Achieving Target Intraocular Pressure, ACTA Ophthalmol Scand Scientific Abstracts, 2002, 457, 80-4.

Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.

Coquelet, P. et al, Successful Photodynamic Therapy Combined with Laser Photocoagulatio in Three Eyes With Classic Subfoveal Choroidal Neovascularisation Affecting Two Patients With Multifocal Choroiditis: Case Reports, Bull. Soc. Beige Ophthalmal, 2002, 69-73, 283.

Di Colo, Giacomo, Controlled Drug Release From Implantable Matrices Based on Hydrophobic Polymers, Biomaterials, 1992, 850-856, 13(12).

Dorlands Medical Dictionary, Analogue, Dorlands Medical Dictionary, 2009, 2 pages, US.

Doucet, O. et al, O/W emulsion and W/O/W multiple emulsion: physical characterization and skin pharmacokinetic comparison in the delivery process of caffeine, Int. J. Cosmetic Scient, 1998, 283-295, 20.

Enyedi, Laura et al, An Intravitreal Device Providing Sustained Release of Cyclosporins and Dexamethason, Current Eye Research, 1996, 549-557.

Epstein, David, Primary Open-Angle Glaucoma, Chandler and Grant's Glaucoma, 1986, 129-181.

Fabbro, Doriano et al, Protein Tyrosine Kinase Inhibitors: New Treatment Modalities?, Current Opinion in Pharmacology, 2002, 374-381, 2.

Fotsis, Theodore et al, The Endogenous Oestrogen Metabolite 2-methoxyoestradiol inhibits Angiogeneses and Suppresses Tumour Growth, Current Opinion in Pharmacology, 1994, 368, 237.

Gennaro, Remington, Ophthalmic Preparations—Vehicles, The Science and Practice of Pharmacy, 2000, 827, 20th Edition.

Gil, Dan et al, Molecular characterization and ocular hypotensive effects of prostanoid EP2 receptors, Exp Eye Res, Sep. 1996, S104—Abstract 5, 63(Suppl 1).

Goel, Sanjay et al, Tyrosine Kinase Inhibitors: A Clinical Perspective, Current Oncology Reports, 2002, 9-19, 4.

Guenther, Lyn, Optimizing Treatment with Topical Tazarotene, Am. J. Clin. Dermotol, 2003, 197-202, 4-3.

Hainsworth, Dean et al, Sustained Release Intravitreal Dexamethasone, Journal of Ocular Pharmacology and Therapeutics, 1996, 57-63, 12-1.

Haluska, Paul et al, Receptor tyrosine kinase inhibitors, Current Opinion in Investigational Drugs, 2001, 280-286, 2-2.

Hare, William et al, Efficacy and Safety of Memantine, an NMDA-Type Open-Channel Blocker, from Reduction of Retinal Injury associated with Experimental Glaucoma in Rat and Monkey, Sur Ophthalmol, 2001, S284-S289, 45—Suppl. 3.

Hashizoe, Mototane et al, Scleral Plug of Biodegradable Polymers for Controlled Drug Release in the Vitreous, Arch Ophthalmol, 1994, 1380-1384, 112.

Haynes, Robert Jr, Adrenocorticotropic Hormone; Adrenocortical Steroids and Their Synthetic Analogs; Inhibitors of the Synthesis and Actions of Adrenocotical Hormones, The Pharmacological Basis of Therapeutics, 1990, 1431-1462, 8th Edition.

Heller, J., Hydrogels in Medicine and Pharmacy, N.A. Peppes ed., 1987, 137-149.

Heller, Jorge, Biodegradable Polymers in Controlled Drug Delivery, Critical Reviews in Therapeutic Drug Carrier Systems, 1987, 39-90, 1 (1).

Herrero-Vanrell, Rocio et al, Biodegradable Microspheres for Vitreoretinal Drug Delivery, Advanced Drug Delivery, 2001, 5-16, 52, US.

Heys, J., A Boussinesq Model of Natural Convection in the Human Eye and the Formation of Krukenberg's Spindle, Annals of Biomedical Engineering, 2002, 392-401, 30.

Higginbotham, Eve et al, One-Year, Randomized Study Comparing Bimatoprost and Timolol in Glaucoma and Ocular Hypertension, Archives of Ophthalmology, Oct. 2002, 1286-1293, 120 (10), US.

Hoyng, Philip et al, Pharmacological Therapy for Glaucoma, Drugs 2000, 2000, 411-434, 59 (3), US.

Hsu, Wei-Cherng et al, Tissue bioengineering for surgical bleb defects: an animal study, Graefe's Archive for Clinical and Experimental Ophthalmology, 2008, 709-717, 246(5).

Hu, D.N. et al, Effects of prostaglandin E2 and EP receptor agonists on human iridial melanocytes in vitro, Invest Ophthalmol Vis Sci, 2001, S832, 42(4), ABS 4467-B486.

Hubbard, Stevan et al, Protein Tyrosine Kinase Structure and Function, Annu. Rev. Biochem., 2000, 373-98, 69.

International Search Report and the Written Opinion of the International Searching Authority for International Application No. PCT/US2010/028584, mailed Aug. 3, 2010.

International Search Report dated Jan. 26, 2012, PCT/US2011/021971.

International Search Report in PCT/US2011/032393.

(56) References Cited

OTHER PUBLICATIONS

Jackanicz, Theodore et al, Polyactic Acid as a Biodegradable Carrier for Contraceptive Steroids, Contraception, 1973, 227-235, 8-3.

Jain, Rajeev et al, Controlled drug delivery by biodegradable poly(ester) devices: different preparative approaches, Drug Dev. Ind. Pharm, 1998, 703-727, 8.

Jain, Rajeev, The manufacturing techniques of various drug loaded biodegradable poly(lactide-co-glycolide) (PLGA) devices, Biomaterials, 2000, 2475-2490, 21.

Jalil, R. et al, Biodegradable poly(lactic acid) and poly(lactide-co-glycolide) microcapsules: problems associated with preparative techniques and release properties, J. Microencapsul., 1990, 297-325, 7(3).

Jalil, R. et al, Microencapsulation using poly (L-lactic acid) II: Preparative variables affecting microcapsule properties, J. Microencapsul., 1990, 25-39, 7(1).

Jalil, R. et al, Microencapsulation using poly(L-lactic acid). I: Microcapsule properties affected by the preparative technique, J. Microencapsul., 1989, 473-484, 6(4).

Jampel, Henry et al, Glaucoma Filtration Surgery in Monkeys Using 5-Fluorouridine in Polyanhydride Disks, Arch Ophthalmol, Mar. 1990, 430-435, 108.

Janoria, Kumar et al, Novel approaches to retinal drug delivery, Expert Opinion on Drug Delivery, Jul. 1, 2007, 376-377, 4.

Janoria, Kumar et al., Novel Approaches to Retinal Drug Delivery, Expert Opinion Drug Delivery, 2007, 371-388, 4 (4).

Kimura, Hideya et al, A New Vitreal Drug Delivery System Using an Implantable Biodegradable Polymeric Device, Invest Ophthalmol Vis Sci, 1994, 2815-2819, 35.

Kivalo, M. et al, Biodegradable tube implants in experimental glaucoma surgery in the rabbit, Journal of Materials Science: Materials in Medicine, 1999, 53-58, 10.

Kochinke, F. et al, Biodegradable Drug Delivery System for Uveitis Treatment, Investigative Ophthalmology & Visual Science, Feb. 15, 1996, 186-B98, 37(3).

Kumar, Janoria et al, Novel Approaches to Retinal Drug Delivery, Expert Opinion on Drug Delivery, 2007, 371-388, 4.

Kwak, Hyung Woo et al, Evaluation of the Retinal Toxicity and Pharmacokinetics of Dexamethasone After Intravitreal Injection, Arch. Ophthalmol, 1992, 259-66, 110.

Ladewig, M.S. et al, Prostaglandin El infusion therapy in dry age-related macular degeneration, Prostaglandins Leukotrienes Essential Fatty Acids, 2005, 251-256, 72.

Lai, Jui-Yang, Biocompatibility Assessment of Gelatin Carriers Used in Corneal Endothelial Cell Delivery, Advances in Condensed Matter and Materials, 2011, 75-96, Chapter 4.

Lai, Jui-Yang, Biocompatibility of chemically cross-liked gelatin hydrogels for ophthalmic use, J. Mater Sci: Mater Med, 2010, 1899-1911, 21.

Lai, Ronald et al, Alpha-2 Adrenoceptor Agonist Protects Retinal Function After Acute Retinal Ischemic Injury in the Rat, Vis Neurosci, 2002, 175-185, 19.

Lee, David et al, Glaucoma Filtration Surgery in Rabbits Using Bioerodible Polymers and 5-Fluorouacil, Ophthalmol, Dec. 1987, 1523-1530, 94-12.

Lee, David et al, The Use of Bioerodible Polymers and 5-Fluorouracils in Glaucoma Filtration Surgery, Ophthalmology & Visual Science, Nov. 1988, 1692-1697, 29-11.

Makadia, Hirenjumar et al, Poly Lactic-co-Glycolic Acid (PLGA) as Biodegradable Controlled Drug Delivery Carrier, Polymers (Basel), 2011, 1377-1397, 3(3).

Marks, R., Topical Tazarotene:Review and Re-Evaluation, Retinoids, 2001, 72-74, 17(3).

Maruquis, Robert et al., Management of Glaucoma: Focus on Pharmacological Therapy, Drugs & Aging, 2005, 1-21, 22 (1).

Maurice, David, Micropharmaceutics of the Eye, Ocular Inflammation Ther., 1983, 97-102, 1.

Mayo Clinic Com, Stargardt's Disease: Can It Be Treated?, May 27, 2008, 2 Pages.

Merck Source, Analogue, Dorland's Medical Dictionary, 2007, 2 pages.

Miller, Robert et al, Degradation Rates of Oral Resorbable Implants (Polyactates and Polyglycolates): Rate Modification with Changes in PLA/PGA Copolymer Ratios, J. Biomed Materials Res, 1977, 711-719, 11.

Miller, Thomas et al, Synthesis and Structure-Activity Profiles of A-Homoestranes, the Estratopones, J. Med. Chem., 1997, 3836-3841, 40.

Moshfeghi, Darius et al, Retinal and Choroidal Vascular Occlusion After Posterior Sub-Tenon Triamcinolone Injection, American Journal of Ophthalmology, 2002, 132-134, vol. 134.

Moss, Kate, Leber's Congenital Amaurosis, TSBVI, Texas Deafblind Outrech, Apr. 27, 2008, 3 Pages, US.

Muther, Philipp Sebastian, Development of a Resorable Anterior Chamber Glaucoma Implant, Dissertation-Rheinland-Westfalen Technical College, May 24, 2006, 1-196.

Nam, Y. S. et al, Protein loaded biodegradable microspheres based on PLGA/protein bioconjugates, J. Microencapsulation, 1999, 625-637, 16(5).

Newman, Nancy, Hereditary Optic Neuropathis: From the Mitochondria to the Optic Nerve, American Journal of Ophthalmology, 2005, 517e1-517e8, 140(3), US.

Nilsson, Siv, PGF $2\alpha$ Increases Uveoscleral Outflow, Invest. Ophthalmol. Vis. Sci, 1987, 284, 28 (Suppl).

Nordstrom et al, Persistence and Adherence With Topical Glaucoma Therapy, American Journal of Ophthalmology, 2005, 598-608, 140, US.

Oculex, Oculex Announces Positive Clinical Results for Posurdex(r) the first biodegradable ocular implant, PR Newswire, Aug. 6, 2002, 1-2.

Olsen, Timothy et al, Human Scleral Permeability: Effects of Age, Cryotherapy, Transcleral Diode Laser, and Surgical Thinning, Invest. Ophthalmol. Vis. Sci., 1995, 1893-1903, 36.

Phillips, Calbert et al, Penetration of Timolol Eye Drops into Human Aqueous Humor: The First Hour, British Journal of Ophthalmology, 1985, 217-218, 69.

Phillips, Tania et al, Efficacy of 0.1% Tazarotene Cream for the treatment of Photodamage, Arch Dermatol, Nov. 2002, 1486-1493, 138(11).

Physician's Desk Reference for Ophthalmic Medicines, 30th Edition, 285-294, 2002.

Pribluda, Victor et al, 2-Methoxyestradiol: An Endogenous Antiangionic and Antiproliferative Drug Candidate, Cancer and Metastasis Reviews, 2000, 173-179, 19.

Quigley, Harry et al, The Mechanism of Optic Nerve Damage in Experimental Acute Intraocular Pressure Elevation, Invest. Ophthalmol. Vis. Sci., 1980, 505-517, 19.

Rao et al, Intraocular Inflammation and Uveitis, Basic and Clinical Science Course; Intraocular Inflammation and Uveitis, 1998-1999, 57-80; 102-103; 152-156, Section 9; Part 2.

Rao et al, Mechanisms of Immune Effector Reactivity, Basic and Clinical Science Course(San Francisco: American Academy of Ophthalmology, 2000-2001, 40-176, 9, Chapter IV.

Renfro, Lisa et al, Ocular Effects of Topical and Systemic Steroids, Dermatologic Clinics, 1992, 505-512, 10.

Schonfeld, David, Lumigan Found Effective in Early Phase 3, Ocul. Surg. News, Mar. 1, 2001, 35, 19(5)1.

Schuettauf, Frank et al, Effects of anti-glaucoma Medications on Ganglion Cell Survival: the DBA/2J Mouse Model, Vision Res., 2002, 2333-2337, 42(20).

Schumacher, Guido et al, The Physiological Estrogen Metabolite 2-Methoxyestradiol Reduced Tumor Growth and Induces Apoptosis in Human Solid Tumors, J Cancer Res Clin Oncol, 2001, 405-410, 127.

Schwartz, Bernard, The Response of Ocular Pressure to Corticosteroids, Ophthamol. Clin. North Am., 1966, 929-989, 6.

Seah, Steve et al, Use of Surodex in Phacotrabeculectomy Surgery, Am J Ophthalmol, May 2005, 927-928, 139(5).

Shi, Weiyun et al, FK506 in a Biodegradable Glycolide-co-Clatide-co-Caprolactone Polymer for Prolongation of Corneal Allograft Survival, Current Eye Research, 2005, 969-976, 30.

(56) References Cited

OTHER PUBLICATIONS

Short, Brian et al, Safety Evaluation of Ocular Drug Delivery Formulations: Techniques and Practical Considerations, Toxicologic Pathology, 2008, 49-62., 36.
Siebold, Earlene et al, Esterified Prostaglandin Shows 'Potent' Promise, Ocular Surgery News, Feb. 1, 1989, pp. 3, 59, 1.
Skalka, Harold et al, Effect of Corticosteroids on Cataract Formation, Arch. Ophthalmol, 1980, 1773-1777, 98.
Smith, Thomas et al, Sustained-Release Subconjunctival 5-Fluorouracil, Ophthalmic Surgery and Laser, Sep. 1996, 763-767, 27-9.
Spaeth, George et al, Steroid-Induced Glaucoma: A. Persistent Elevatioin of Intraocular Pressure B. Hisopathological Aspects, Th. Am. Ophth. Soc., 1977, 353-381, vol. LXXV, US.
Starr, Michael, Further Studies on the Effects of Prostagladin on Intraocular Pressure in the Rabbit, Exp. Eye Res., 1971, 170-177, 11.
Stewart, William et al, The Efficacy and Safety of Latanoprost 0.005% Once Daily Versus Brimonidine 0.2% Twice Daily in Open-Angle Glaucoma or Ocular Hypertension, Am J Ophthalmol, May 2001, 631-635, 131.
Tan, D.T.H., Randomized Clinical Trial of a New Dexamethasone Delivery System (Surodex) for Treatment of Post-Cataract Surgery Inflammation, Ophthalmology, Feb. 1999, 223-231, 106 (2), US.
Tan, Donald et al, Randomized Clinical Trial of a New Dexamethasone Delivery System (Surodex) for Treatment of Post-Cataract Surgery Inflammation, Ophthalmology, Feb. 1999, 223-231, 106 (2).
Tan, Donald et al, Randomized Clinical Trial of Surodex Steroid Drug Delivery System for Cataract Surgery: Anterior Versus Posterior Placement of Two Surodex in the Eye, Ophthalmology, Dec. 2001, 2172-2181, 108(12).
Tazarotene, Drugs Future, 208-209-2003.
Theng, Julian et al, Pharmacokinetic and Toxicity Study of an Intraocular Cyclosporine DDS in the Anterior Segment of Rabbit Eyes, Invest Ophthalmol Vis Sci, Nov. 2003, 4895-4899, 44(11).
Theng, Julian et al, Pharmacokinetic and Toxicity Study of Intraocular Cyclosporine DDS in the Anterior Segment of Rabbit Eyes, Investigative Ophthalmology & Visual Science, Nov. 2003, 4895-4899, 44 (11), US.
Tracy, M.A. et al, Factors Affecting the Degradation Rate of Poly(actide-co-glycolide) Microspheres in Vivo and in Vitro, Biomatenals, 1999, 1057-1062, 20.
U.S. Appl. No. 13/861,688, filed Apr. 12, 2013.
U.S. Appl. No. 10/246,884, filed Sep. 18, 2002.
U.S. Appl. No. 10/259,703, filed Sep. 27, 2002.
U.S. Appl. No. 10/327,018, filed Dec. 20, 2002.
U.S. Appl. No. 10/340,237, filed Jan. 9, 2003.
U.S. Appl. No. 10/836,880, filed Apr. 30, 2004.
U.S. Appl. No. 10/836,904, filed Apr. 30, 2004.
U.S. Appl. No. 10/836,908, filed Apr. 30, 2004.
U.S. Appl. No. 10/837,143, filed Apr. 30, 2004.
U.S. Appl. No. 10/837,142, filed Apr. 30, 2004.
U.S. Appl. No. 10/837,260, filed Apr. 30, 2004.
U.S. Appl. No. 10/837,291, filed Apr. 30, 2004.
U.S. Appl. No. 10/837,348, filed Apr. 30, 2004.
U.S. Appl. No. 10/837,356, filed Apr. 30, 2004.
U.S. Appl. No. 10/837,361, filed Apr. 20, 2004.
U.S. Appl. No. 10/837,379, filed Apr. 30, 2004.
U.S. Appl. No. 10/966,764, filed May 12, 2005.
U.S. Appl. No. 11/039,192, filed Aug. 18, 2005.
U.S. Appl. No. 11/118,519, filed Apr. 29, 2005.
U.S. Appl. No. 11/303,462, filed Dec. 15, 2005.
U.S. Appl. No. 11/368,845, filed Mar. 6, 2006.
U.S. Appl. No. 11/371,118, filed Mar. 8, 2006.
U.S. Appl. No. 11/395,019, filed Mar. 31, 2006.
U.S. Appl. No. 11/455,392, filed Dec. 20, 2007.
U.S. Appl. No. 11/552,835, filed Apr. 24, 2008.
U.S. Appl. No. 11/565,917, filed Dec. 1, 2006.
U.S. Appl. No. 11/741,366, filed Sep. 27, 2007.
U.S. Appl. No. 11/859,627, filed Mar. 26, 2009.
U.S. Appl. No. 11/952,927, filed Dec. 7, 2007.
U.S. Appl. No. 11/952,938, filed Dec. 7, 2007.
U.S. Appl. No. 12/028,762, filed Feb. 8, 2008.
U.S. Appl. No. 12/028,763, filed Feb. 8, 2008.
U.S. Appl. No. 12/255,497, filed Oct. 21, 2008.
U.S. Appl. No. 12/259,153, filed Oct. 27, 2008.
U.S. Appl. No. 12/355,709, filed Jan. 16, 2009.
U.S. Appl. No. 12/411,250, filed Mar. 25, 2009.
U.S. Appl. No. 12/761,765, filed Apr. 16, 2010.
U.S. Appl. No. 13/011,467, filed Jan. 21, 2011.
U.S. Appl. No. 13/152,780, filed Jun. 3, 2011.
U.S. Appl. No. 13/466,752, filed May 8, 2012.
U.S. Appl. No. 13/466,804, filed May 8, 2012.
U.S. Appl. No. 13/511,548, filed May 23, 2012.
U.S. Appl. No. 60/567,423, filed Apr. 30, 2004.
U.S. Appl. No. 60/567,339, filed Apr. 30, 2004.
U.S. Appl. No. 61/287,078, filed Dec. 16, 2009.
U.S. Appl. No. 61/297,660, filed Jan. 22, 2010.
U.S. Appl. No. 10/836,911, filed Apr. 30, 2004.
U.S. Appl. No. 11/552,630, filed Feb. 7, 2008.
United States Board of Appeals and Interferences decision on appeal in Ex parte Huang et al, Appeal No. 2009-013914, U.S. Appl. No. 10/340,237, mailed Sep. 21, 2010.
United States Board of Patent and Interferences decision on appeal in Ex parte Huang et al, Appeal No. 2010-006865, U.S. Appl. No. 10/836,880, mailed Sep. 28, 2010.
United States Board of Patent Appeals and Interferences decision on appeal in Ex parte Hughes et al, Appeal No. 2010-004999, U.S. Appl. No. 10/836,911, mailed Oct. 25, 2010.
United States Board of Patent Appeals and Interferences on appeal in Ex parte Hughes et al, Appeal No. 2011-003859, U.S. Appl. No. 11/116,698, mailed Aug. 1, 2011.
United States Pharmacopeia, The National Formulary, USP23, 1995, 1790-1798, 18.
U.S. Appl. No. 11/118,519, filed Apr. 29, 2004.
Wadood, Azfar et al, Safety and Efficacy of a Dexamethasone Anterior Segment Delivery System in Patients After Phacoemulsification, Journal of Cataract and Refractive Surgery, Apr. 2004, 761-768, 30.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Wheeler, Larry et al, From the Lab to the Clinic: Activation of an Alpha-2 Agonist Pathway is Neuroprotective in Models of Retinal and Optic Nerve Injury, Eur. J. Ophthalmology, 1999, S17-S22, 9 (1).
Wheeler, Larry et al, Role of Alpha-2-Agonist in Neuroprotection, Sur Ophthalmol, 2003, S47-S51, 48(Suppl 1).
Wheeler, Larry, Experimental Study of Agents with Potential Neuroprotective Properties, Acta Ophthalmol Scand, 1999, 27-28, 77.
Wine, N.A. et al, The Ocular Uptake of Subconjunctivally Injected C14 Hydrocortisone, Am. J. Ophthalmol., 1964, 362-366, 58.
Wischke, Christian et al, Principles of Encapsulating Hydrophobic Drugs in PLA/PLGA Microparticles, International Journal of Pharmaceutics, 2008, 298-327, 364.
Woldemussie, Elizabeth et al, Neuroprotection Effects of Memantine in Different Retinal Injury Models of Glaucoma, J Glaucoma, 2002, 474-480, 11(6).
Woldemussie, Elizabeth, Neuroprotection of Retinal Ganglion Cells in Experimental Models of Glaucoma, Minerva Ophthalmol, 2000, 71-78, 42(2).
Woodward, David et al, AGN 192024 (LumiganR): A Synthetic Prostamide Analog that Lowers Primate Intraocular Pressure by Virtue of Its Inherent Pharmacological Activity, ARVO, 2002, 1 page (Abstract), 43.
Woodward, David et al, Eicosanoid Receptors: Pharmacology and Ocular Distribution, Exp Eye Res, Sep. 1996, S23—Abstract 2, 63(Suppl 1).
Woodward, David et al, Fixed-Combination and Emerging Glaucoma Therapies, Expert. Opin. Emerging Drugs, 2007, 313-327, 12(2), US.

(56) References Cited

OTHER PUBLICATIONS

Woodward, David et al, The molecular biology and ocular distribution of prostanoid receptors, Surv Ophthalmol, Feb. 1997, S15-S21, 41(Suppl 2).

Woodward, David et al, The Pharmacology of Bimatoprost (LumiganTM), Surv Ophthalmol, 2001, S337-S345, Suppl 4.

Woodward, et al., "Fixed-Combination and Emerging Glaucoma Therapies", Expert Opinion on Emerging Drugs, 2007, 313-327, 12 (2).

Zhou, Tianhong et al, Development of a Multiple-Drug Delivery Implant for Intraocular Management of Proliferative Vitreoretinopathy, Journal of Controlled Release, 1998, 281-295, 55.

Zhou, Tianhong et al, Development of a Multiple-Drug Delivery Implant for Intraocular Management of Proliferative Vitreoretinopathy, Journal of Controlled Release, 1998, 281-295, 55, US.

The Advanced Glaucoma Intervention Study (AGIS): 7. The relationship between control of intraocular pressure and visual field deterioration. The AGIS Investigators, no authors listed, AM J. Ophthalmol. Oct. 2000; 130(4):429-40, printed from http://ncbi.nlm.nih.gov/pubmed/11024415, 2 pages, abstract only.

* cited by examiner

AGN 192024

15β AGN 192024

5,6-trans AGN 192024 isomer

C1 Acid of AGN 192024 riphenylphoshpine Oxide (TPPO)

15-Keto AGN 192024 (Formerly "Impurity A)

METHOD OF MAKING OIL-IN-OIL EMULSIFIED POLYMERIC IMPLANTS CONTAINING A HYPOTENSIVE LIPID

CROSS-REFERENCE TO RELATED APPLICATIONS

This application is a divisional of copending U.S. patent application Ser. No. 13/861,688, filed on Apr. 12, 2013, which is a continuation of U.S. patent application Ser. No. 13/152,780, filed on Jun. 3, 2011, and now U.S. Pat. No. 8,445,027, which is a divisional of U.S. application Ser. No. 11/303,462, filed on Dec. 15, 2005, and now U.S. Pat. No. 7,993,634, which is a continuation-in-part of U.S. application Ser. No. 10/837,260, filed Apr. 30, 2004, and now U.S. Pat. No. 7,799,336, the entire contents of which are hereby incorporated by reference.

BACKGROUND

The present invention generally relates to devices and methods to treat an eye of a patient, and more specifically to intraocular implants or microparticles that provide extended release of a therapeutic agent to an eye in which the implant is placed to treat ocular hypertension, such as by reducing or at least maintaining intraocular pressure, and to methods of making and using such implants.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical beta-adrenoreceptor antagonists have traditionally been the drugs of choice for treating glaucoma.

Prostaglandins were earlier regarded as potent ocular hypertensives: however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla., CRC Press Inc., 1985, pp. 231-252; and Bito, L. Z., Applied Pharmacology in the Medical Treatment of Glaucomas Drance, S. M. and Neufeld. A. H. eds., New York. Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., Invest Ophthalmol. Vis. Sci. 28(suppl), 284 (1987)].

The isopropyl ester of $PGF_{2\alpha}$ has been shown to have significantly greater hypotensive potency than the parent compound, which was attributed to its more effective penetration through the cornea. In 1987, this compound was described as "the most potent ocular hypotensive agent ever reported." [See, for example, Bito, L. Z., Arch. Ophthalmol. 105, 1036 (1987), and Siebold et al., Prodrug 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain prostaglandins and their analogs and derivatives, such as the $PGF_{2\alpha}$ derivative latanoprost, sold under the trademark Xalatan®, have been established as compounds useful in treating ocular hypertension and glaucoma. However, latanoprost, the first prostaglandin approved by the United States Food And Drug Administration for this indication, is a prostaglandin derivative possessing the undesirable side effect of producing an increase in brown pigment in the iris of 5-15% of human eyes. The change in color results from an increased number of melanosomes (pigment granules) within iridial melanocytes. See e.g., Watson et al., Ophthalmology 103:126 (1996). While it is still unclear whether this effect has additional and deleterious clinical ramifications, from a cosmetic standpoint alone such side effects are undesirable.

Certain phenyl and phenoxy mono, tri and tetra nor prostaglandins and their 1-esters are disclosed in European Patent Application 0,364,417 as useful in the treatment of glaucoma or ocular hypertension.

In a series of United States patent applications assigned to Allergan, Inc. prostaglandin esters with increased ocular hypotensive activity accompanied with no or substantially reduced side-effects are disclosed. U.S. patent application Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in U.S. Ser. No. 357,394 (filed May 25, 1989). Similarly, 11,15-9,15- and 9,11-diesters of prostaglandins, for example 11,15-dipivaloyl $PGF_{2\alpha}$ are known to have ocular hypotensive activity. See U.S. Ser. No. 385.645 filed Jul. 27, 1990, now U.S. Pat. Nos. 4,494,274; 584,370 which is a continuation of U.S. Ser. No. 386,312, and U.S. Ser. No. 585.284, now U.S. Pat. No. 5,034,413 which is a continuation of U.S. Ser. No. 388,834, where the parent applications were filed on Jul. 27, 1989.

Woodward et at U.S. Pat. Nos. 5,688,819 and 6,403,649 disclose certain cyclopentane heptanoic acid, 2-cycloalkyl or arylalkyl compounds as ocular hypotensives. These compounds, which can properly be characterized as hypotensive lipids, are effective in treating ocular hypertension.

As one example, the prostamide analog, bimatoprost, has been discovered to be effective in reducing intraocular pressure possibly by increasing the aqueous humour outflow of an eye (Woodward et al., AGN 192024 (Lumigan®): A Synthetic Prostamide Analog that Lowers Primate Intraocular Pressure by Virtue of its Inherent Pharmacological Activity. ARVO 2002; (CD-ROM):POS; Chen et al., Lumigan®: A Novel Drug for Glaucoma Therapy, Optom In Pract, 3:95-102 (2002); Coleman et al., A 3-Month Randomized Controlled Trial of Bimatoprost (LUMIGAN) versus Combined Timolo and Dorzolamide (Cosopt) in Patients with Glaucoma or Ocular Hypertension, Ophthalmology 110(12): 2362-8 (2003); Brubaker, Mechanism of Action of Bimatoprost (Lumigan™), Surv Ophthalmol 45 (Suppl 4):S347-S351 (2001); and Woodward et al., The Pharmacology of Bimatoprost (Lumigan™), Surv Ophthalmol 45 (Suppl 4) S337-S345 (2001).

Bimatoprost is an analog (e.g., a structural derivative) of a naturally occurring prostamide. Bimatoprost's chemical name is (Z)-7-[(1R,2R,3R,5S)-3,5-Dihydroxy-2-(1E,3S)-3-hydroxy-5-phenyl-1-pentenyl)cyclopentyl]-5-N-ethylheptenamide, and it has a molecular weight of 415.58. It's molecular formula is $C_{25}H_{37}NO_4$. Bimatoprost is available in a topical ophthalmic solution under the tradename Lumigan® (Allergan, Inc.). Each mL of the solution contains 0.3 mg of bimatoprost as the active agent, 0.05 mg of benzalkonium chloride (BAK) as a preservative, and sodium chloride, sodium phosphate, dibasic; citric acid; and purified water as inactive agents.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

It would be advantageous to provide eye implantable drug delivery systems, such as intraocular implants, and methods of using such systems, that are capable of releasing a therapeutic agent, such as a hypotensive agent, at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements that may be placed in an eye. The present systems and methods advantageously provide for extended release times of one or more therapeutic agents. Thus, the patient in whose eye the implant or population of implants has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about two and about six months after receiving an implant. Such extended release times facilitate obtaining successful treatment results.

Intraocular implants in accordance with the disclosure herein comprise a therapeutic component and a drug release sustaining component associated with the therapeutic component. In accordance with the present invention, the therapeutic component comprises, consists essentially of, or consists of, a prostamide component, such as a prostamide derivative that is effective in reducing or maintaining a reduced intraocular pressure in a hypertensive eye. The drug release sustaining component is associated with the therapeutic component to sustain release of an amount of the prostamide component into an eye in which the implant is placed. The amount of the prostamide component is released into the eye for a period of time greater than about one week after the implant is placed in the eye and is effective in treating or reducing at least one symptom of an ocular condition of an eye. Advantageously, the present intraocular implants may be effective in relieving a hypertensive eye by reducing the intraocular pressure of the eye or maintaining the intraocular pressure at a reduced level.

Embodiments of the present implants can be understood from the following description and claims.

In one embodiment, the intraocular implants comprise prostamide component and a biodegradable polymer matrix. The prostamide component is associated with a biodegradable polymer matrix that releases drug at a rate effective to sustain release of an amount of the prostamide component from the implant effective to treat an ocular condition. The intraocular implant is biodegradable or bioerodible and provides a sustained release of the prostamide component in an eye for extended periods of time, such as for more than one week, for example for about three months or more and up to about six months or more.

The biodegradable polymer component of the foregoing implants may be a mixture of biodegradable polymers, wherein at least one of the biodegradable polymers is a polylactic acid polymer having a molecular weight less than 64 kiloDaltons (kD). Additionally or alternatively, the foregoing implants may comprise a first biodegradable polymer of a polylactic acid, and a different second biodegradable polymer of a polylactic acid. Furthermore, the foregoing implants may comprise a mixture of different biodegradable polymers, each biodegradable polymer having an inherent viscosity in a range of about 0.2 deciliters/gram (dl/g) to about 1.0 dl/g.

The prostamide component of the implants disclosed herein may include prostamide derivatives, such as a prostamide analog, that are effective in treating ocular conditions. One example of a suitable prostamide derivative is bimatoprost or a salt thereof. In addition, the therapeutic component of the present implants may include one or more additional and different therapeutic agents that may be effective in treating an ocular condition.

A method of making the present implants involves combining or mixing the prostamide component with a biodegradable polymer or polymers. The mixture may then be extruded or compressed to form a single composition. The single composition may then be processed to form individual implants suitable for placement in an eye of a patient.

A method of making the present implants may also include using an oil-in-oil emulsion process to form the implants. Such methods may be particularly useful in forming microparticles and the like. Thus, an embodiment of the present invention relates to methods of making microparticles using an oil-in-oil emulsion process and microparticles so produced, as described herein.

The implants, including a population of microparticles, may be placed in an ocular region to treat a variety of ocular conditions. For example, the implants may be effective in reducing ocular hypertension, and thereby may be effective in reducing at least one symptom of an ocular condition associated with an increased intraocular pressure.

Kits in accordance with the present invention may comprise one or more of the present implants, and instructions for using the implants. For example, the instructions may explain how to administer the implants to a patient, and types of conditions that may be treated with the implants.

The present invention also encompasses the use of the present implants in treating a patient, such as in treating one or more of the conditions or diseases set forth herein, as well as medicaments, which are oil-in-oil emulsified implants or microparticles, for treating an ocular condition of a patient. The invention also encompasses the use of a prostamide component and a polymeric component, as described herein, in the manufacture of a medicament for treating a patient.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

BRIEF DESCRIPTION OF THE DRAWINGS

FIG. 38 is a chromatogram of non-sterilized bimatoprost microparticles.

DESCRIPTION

Figure 1:
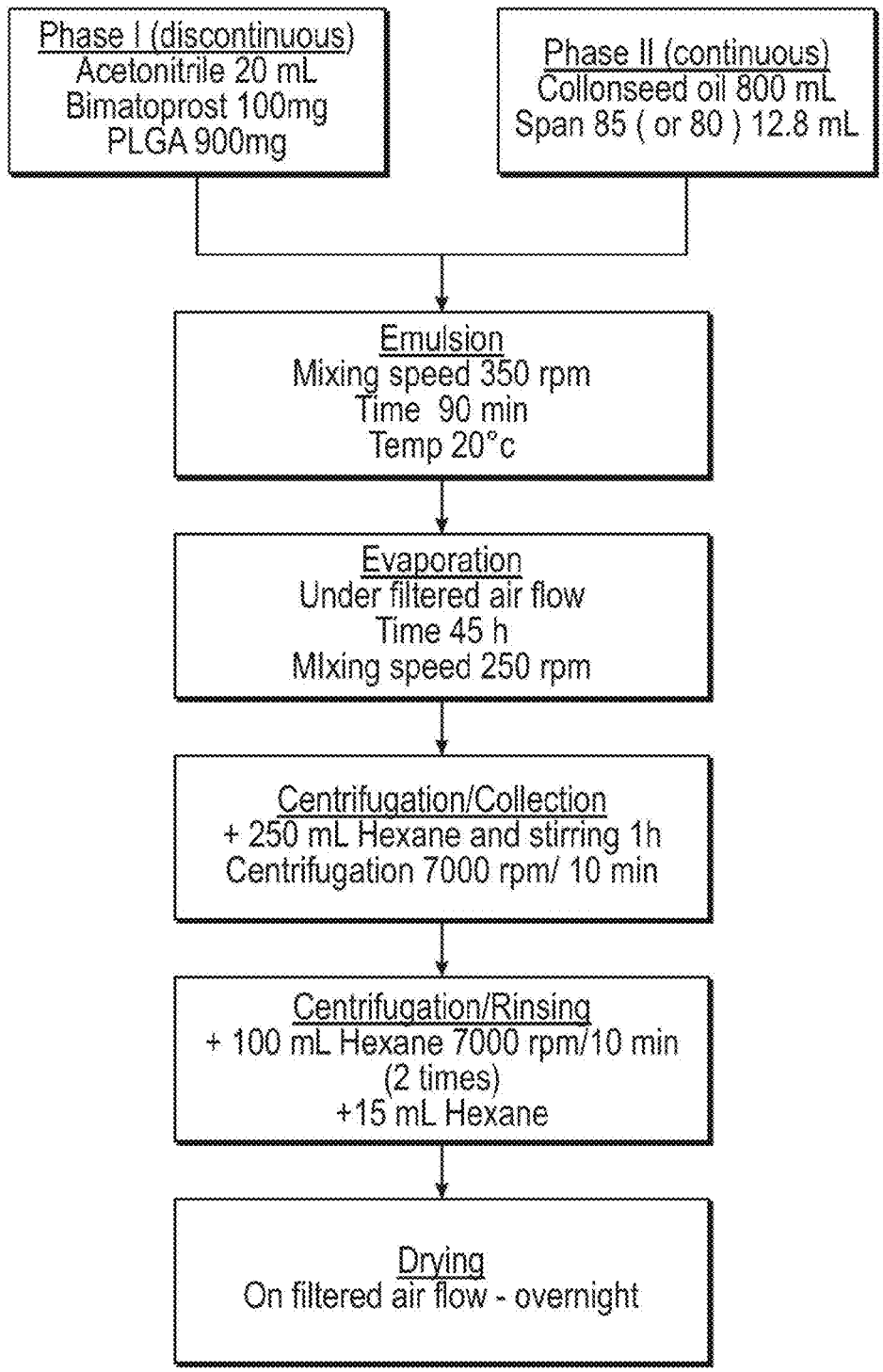
FIG. 1 is flow chart of a method of making microspheres.

As described herein, controlled and sustained administration of a therapeutic agent through the use of one or more intraocular implants, including microparticles or microparticle implants, may improve treatment of undesirable ocular conditions. The implants and microparticles comprise a pharmaceutically acceptable polymeric composition and are formulated to release one or more pharmaceutically active agents, such as a prostamide, a prostamide derivative, such as a prostamide analog, or other intraocular pressure lowering agent, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or repeated administration of topical drops.

An intraocular implant or microparticle in accordance with the disclosure herein comprises a therapeutic component and a drug release sustaining component associated with the therapeutic component. In accordance with the present invention, the therapeutic component comprises, consists essentially of, or consists of, a prostamide component. The drug release sustaining component is associated with the therapeutic component to sustain release of an effective amount of the prostamide component into an eye in which the implant or microparticle is placed. The amount of the prostamide component is released into the eye for a period of time greater than about one week after the implant or microparticle is placed in the eye, and is effective in treating or reducing a symptom of an ocular condition.

DEFINITIONS

For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye. Implants refer to elements that have maximum dimensions that are on the order of millimeters as well as elements that have maximum dimensions on the order of micrometers. Micrometer sized elements may be understood to be microparticles. Microparticles have a maximum dimension, such as diameter or length, less than 1 mm. For example, microparticles can have a maximum dimension less than about 500 µm. Microparticles may also have a maximum dimension no greater than about 200 µm, or may have a maximum dimension from about 30 µm to about 50 µm, among other sizes.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthamically acceptable, and are provided in a form that does not cause adverse reactions when the implant is placed in an eye.

As used herein, a "prostamide component" refers to a portion of an intraocular implant that comprises one or more prostamides, one or more prostamide derivatives, such as a prostamide analog, salts thereof, and mixtures thereof. A prostamide derivative is a compound that contains the essential elements of the prostamide from which it is derived in order to provide a therapeutic effect. A prostamide derivative includes prostamide analogs, and can be identified using any conventional methods known by persons of ordinary skill in the art used to evaluate the efficacy of a prostamide. For example, therapeutically effective prostamide derivatives can be identified by applying the prostamide derivative to an eye with increased intraocular pressure, and evaluating whether the intraocular pressure decreases after the application. A prostamide component may also include one or more prostaglandin analogs.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitroretinopathy (PVR), retinal arterial occlusive disease, retinal detachment, uveltic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue. A treatment is usually effective to reduce at least one symptom of an ocular condition, ocular injury or damage.

The term "therapeutically effective amount" as used herein, refers to the level or amount of agent needed to treat an ocular condition, or reduce or prevent ocular injury or damage without causing significant negative or adverse side effects to the eye or a region of the eye. In view of the above, a therapeutically effective amount of a therapeutic agent such as a prostamide or prostamide derivative, is an amount that is effective in reducing at least one symptom of an ocular condition.

Intraocular implants have been developed which can release drug loads over various time periods. These implants, which when inserted into an eye, such as the vitreous of an eye, provide therapeutic levels of a prostamide component for extended periods of time (e.g., for about 1 week or more). The disclosed implants are effective in treating ocular conditions, such as ocular conditions associated with elevated intraocular pressure, and more specifically in reducing at least one symptom of glaucoma.

Methods for producing intraocular implants have also been developed. For example, the present invention encompasses therapeutic polymeric microparticles and methods of making and using such microparticles. As disclosed herein, the microparticles may be oil-in-oil emulsified microparticles.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises a prostamide component associated with the biodegradable polymer matrix. The matrix degrades at a rate effective to sustain release of an amount of the prostamide component for a time greater than about one week from the time in which the implant is placed in ocular region or ocular site, such as the vitreous of an eye.

The prostamide component of the implant includes one or more types of prostamides, prostamide derivatives, salts thereof, and mixtures thereof. In certain implants, the prostamide component comprises a compound having the formula (I)

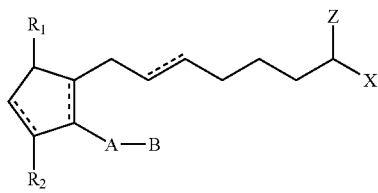

wherein the dashed bonds represent a single or double bond which can be in the cis or trans configuration. A is an alkylene or alkenylene radical having from two to six carbon atoms, which radical may be interrupted by one or more oxide radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of $-OR^4$ and $-N(R^4)_2$ wherein $R^4$ is selected from the group consisting of hydrogen, a lower alkyl radical having from one to six carbon atoms,

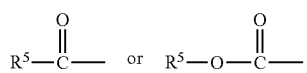

wherein $R^5$ is a lower alkyl radical having from one to six carbon atoms; Z is =O or represents 2 hydrogen radicals; one of $R_1$ and $R_2$ is =O, $-OH$ or a $-O(CO)R_6$ group, and the other one is $-OH$ or $-O(CO)R_6$, or $R_1$ is =O and $R_2$ is H, wherein $R_6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not $-OR^4$.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In more specific implants, the compound of the prostamide component has the following formula (II)

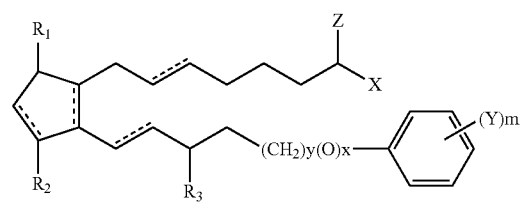

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is =O, $-OH$ or $-O(CO)R_6$.

In additional implants, the compound of the prostamide component has the following formula (III)

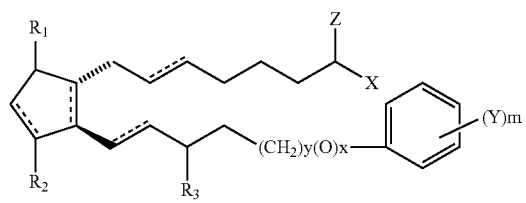

wherein hatched lines indicate the α configuration and solid triangles indicate the β configuration.

In certain implants, the compound of the prostamide component has the following formula (IV)

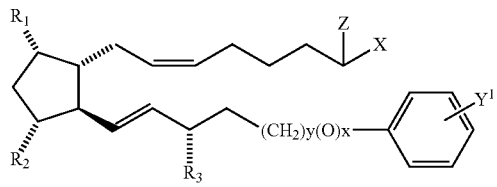

wherein $Y^1$ is Cl or trifluoromethyl, such as the compound having the following formula (V)

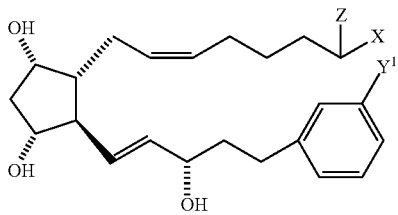

and the 9- and/or 11- and/or 15 esters thereof.

In at least one type of intraocular implant, the prostamide component comprises a compound having the following formula (VI)

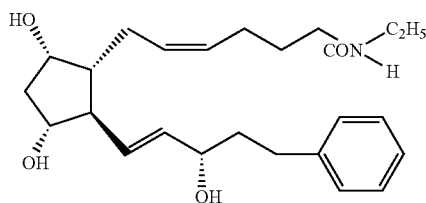

The compound having the formula VI is also known as bimatoprost and is publicly available in a topical ophthalmic solution under the tradename, Lumigan® (Allergen, Inc., CA).

Thus, the implant may comprise a therapeutic component which comprises, consists essentially of, or consists of bimatoprost, a salt thereof, or mixtures thereof.

The prostamide component may be in a particulate or powder form and it may be entrapped by the biodegradable polymer matrix. Usually, prostamide particles will have an effective average size less than about 3000 nanometers. In certain implants, the particles may have an effective average particle size about an order of magnitude smaller than 3000 nanometers. For example, the particles may have an effective average particle size of less than about 500 nanometers, In additional implants, the particles may have an effective average particle size of less than about 400 nanometers, and in still further embodiments, a size less than about 200 nanometers.

The prostamide component of the implant is preferably from about 10% to 90% by weight of the implant. More preferably, the prostamide component is from about 20% to about 80% by weight of the implant. In a preferred embodiment, the prostamide component comprises about 20% by weight of the implant (e.g., 15%-25%). In another embodiment, the prostamide component comprises about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy. e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implant's surface, dissolution, diffusion through porous channels of the hydrated polymer and erosion. Erosion can be bulk or surface or a combination of both. As discussed herein, the matrix of the intraocular implant may release drug at a rate effective to sustain release of an amount of the prostamide component for more than one week after implantation into an eye. In certain implants, therapeutic amounts of the prostamide component are released for no more than about 30-35 days after implantation. For example, an implant may comprise bimatoprost, and the matrix of the implant degrades at a rate effective to sustain release of a therapeutically effective amount of bimatoprost for about one month after being placed in an eye. As another example, the implant may comprise bimatoprost, and the matrix releases drug at a rate effective to sustain release of a therapeutically effective amount of bimatoprost for more than forty days, such as for about six months.

One example of the biodegradable intraocular implant comprises an prostamide component associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the prostamide component for a time period greater than about one month from the time the implant is placed in an eye.

Another example of a biodegradable intraocular implant comprises an prostamide component associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. Additional implants may comprise biodegradable polymers that have an inherent viscosity between about 0.2 dl/g and 0.5 dl/g. The inherent viscosities identified above may be determined in 0.1% chloroform at 25° C.

One particular implant comprises bimatoprost associated with a combination of two different polylactide polymers. The bimatoprost is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant may be effective in releasing the bimatoprost for more than two months. The implant is provided in the form of a rod or a filament produced by an extrusion process.

The release of the prostamide component from the intraocular implant comprising a biodegradable polymer matrix may include an initial burst of release followed by a gradual increase in the amount of the prostamide component released, or the release may include an initial delay in release of the prostamide component followed by an increase in release. When the implant is substantially completely degraded, the percent of the prostamide component that has been released is about one hundred. Compared to existing implants, the implants disclosed herein do not completely release, or release about 100% of the prostamide component, until after about one week of being placed in an eye.

It may be desirable to provide a relatively constant rate of release of the prostamide component from the implant over the life of the implant. For example, it may be desirable for the prostamide component to be released in amounts from about 0.01 μg to about 2 μg per day for the life of the implant. However, the release rate may change to either increase or decrease depending on the formulation of the biodegradable polymer matrix. In addition, the release profile of the prostamide component may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the prostamide component, may be distributed in a non-homogenous pattern in the matrix. For example, the implant may include a portion that has a greater concentration of the prostamide component relative to a second portion of the implant.

The intraocular implants disclosed herein may have a size of between about 5 μm and about 10 mm, or between about 10 μm and about 1 mm for administration with a needle, greater than 1 mm, or greater than 2 mm, such as 3 mm or up to 10 mm, for administration by surgical implantation. For needle-injected implants, the implants may have any appropriate length so long as the diameter of the implant permits the implant to move through a needle. For example, implants having a length of about 6 mm to about 7 mm have been injected into an eye. The implants administered by way of a needle should have a diameter that is less than the inner diameter of the needle. In certain implants, the diameter is less than about 500 μm. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of the prostamide component, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the prostamide or prostamide derivatives included in the intraocular implants disclosed herein, the intraocular implants may also include one or more additional ophthalmically acceptable therapeutic agents. For example, the implant may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chlorcyclizine, thonzylamine, and derivatives thereof.

Examples of antibiotics include without limitation, cefazolin, cephradine, cefactor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperadcillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, flurometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valaciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha-2 adrenergic receptor agonists, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

Some of the present implants may comprise a prostamide component that comprises a combination of two or more different prostamide derivatives. One implant may comprise a combination of bimatoprost and latanoprost. Another implant may comprise a combination of bimatoprost and travoprost.

As discussed herein, the present implants may comprise additional therapeutic agents. For example, one implant may comprise a combination of bimatoprost and a beta-adrenergic receptor antagonist. More specifically, the implant may comprise a combination of bimatoprost and Timolol®. Or, an implant may comprise a combination of bimatoprost and a carbonic anyhdrase inhibitor. For example, the implant may comprise a combination of bimatoprost and dorzolamide (Trusopt®).

In addition to the therapeutic component, the intraocular implants disclosed herein may include or may be provided in compositions that include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight. In at least one of the present implants, a benzylalkonium chloride preservative is provided in the implant, such as when the prostamide component consists essentially of bimatoprost.

In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the prostamide component in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant comprising bimatoprost and a biodegradable polymer matrix is able to release or deliver an amount of bimatoprost between about 0.1 mg to about 0.5 mg for about 3-6 months after implantation into the eye. The implant may be configured as a rod or a wafer. A rod-shaped implant may be derived from filaments extruded from a 720 μm nozzle and cut into 1 mg size. A wafer-shaped implant may be a circular disc having a diameter of about 2.5 mm, a thickness of about 0.127 mm, and a weight of about 1 mg.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

Another method comprises using an oil-in-oil emulsion process to produce the present implants, including the microparticle implants or microparticles.

In one embodiment, a method for producing therapeutic polymeric microparticles comprises encapsulating a prostamide component with a polymeric component to form a population of prostamide-encapsulated microparticles by an oil-in-oil emulsion process. Such microparticles are effective in treating one or more ocular conditions, as described herein, and are suitable for administration to a patient into the vitreous or outside of the vitreous of a patient's eye. The therapeutic activity of the prostamide component remains stable during storage of the implants which may be attributed to the particular encapsulated form of the implants.

In more detail, a method of forming microparticles comprises forming an oil-in-oil emulsion containing the prostamide component and the polymeric component. For example, the method may include mixing or combining a plurality, such as two or more, non-aqueous liquid compositions to form an emulsion, in one embodiment, a first composition may comprise an organic solvent, and a second composition may comprise an oil. At least one of the compositions contains the prostamide component, the polymeric component, or the prostamide component and the polymeric component. The method also comprises drying the emulsion to form a dried emulsion product. The drying can be achieved using one or more techniques to remove the liquid from the emulsified product. For example, the drying process can include increasing the temperature of or near the emulsified product to facilitate evaporation of the liquid, can include the use of a vacuum to facilitate removal of the liquid, can include centrifugation to separate solid from the liquid, and combinations thereof.

The dried emulsion product can then be contacted with a solvent to form a solvent containing composition. Adding a solvent to the dried emulsion product, or otherwise contacting the product with the solvent results in the product being suspended in a volume of the liquid solvent. The contacting can include a step of stirring or mixing the combination of the solvent and dried emulsion product to form a suspension of the dried emulsion product in the solvent. The suspension can include particles of the dried emulsion product. For example, particles of various sizes and shapes, including microparticles and or microspheres.

After forming the solvent containing composition, the method can comprise removing the solvent from the solvent-containing composition to form a population of microparticles that comprise the prostamide component and the polymeric component. The removing can include one or more steps of centrifuging and/or rinsing intermediate compositions, and can include one or more steps of drying the resulting composition. The resulting products are encapsulated microparticles or microimplants that comprise a prostamide component encapsulated by a polymeric component, such as a biodegradable polymer coating.

As discussed herein, the prostamide component can comprises a single type of prostamide derivative or derivatives. In certain embodiments, the prostamide component comprises at least one prostamide derivative selected from the group consisting of bimatoprost, salts thereof, and mixtures thereof. In a further embodiment, the prostamide component consists essentially of bimatoprost.

In additional embodiments, the prostamide component can comprise combinations of two or more different prostamide derivatives, such as a combination of bimatoprost and latanoprost, bimatoprost and travoprost, and the like.

The present methods are effective in producing encapsulated prostamide component microparticles that maintain or preserve a substantial portion, if not all, of the therapeutic activity after a terminal sterilization procedure. It can be understood, that the present methods may also comprise a step of terminally sterilizing the microparticles. The microparticles can be sterilized before packaging or in their packaging. Sterilization of packages containing the present microparticles or implants is often preferred. The method may comprise exposing the present microparticles or implants to sterilizing amounts of gamma radiation, e-beam radiation, and other terminal sterilization products. In one embodiment, a method may comprise a step of exposing the present microparticles to gamma radiation at a dose of about 26 kGy.

As discussed herein, the polymeric component recited in the present method may comprise a biodegradable polymer or biodegradable copolymer. In at least one embodiment, the polymeric component comprises a poly (lactide-co-glycolide) PLGA copolymer. In a further embodiment, the PLGA copolymer has a lactide/glycolide ratio of 75/25. In a still further embodiment, the PLGA copolymer has at least one of a molecular weight of about 63 kilodaltons and an inherent viscosity of about 0.6 dL/g.

The present methods may also comprise a step of forming a first composition which comprises a prostamide component, a polymeric component, and an organic solvent, and a step of forming a second oil-containing composition, and mixing the first composition and the second oil-containing composition.

The present methods may also comprise evaporating the oil-in-oil emulsion to form an evaporated product, as described herein.

Further, the methods may comprise a step of suspending the evaporated product in a solvent before removing the solvent from the solvent containing composition. Such a step can be understood to be a way of forming a suspension.

As one example, a method of forming encapsulated bimatoprost biodegradable microparticles comprises forming an oil-in-oil emulsion comprising the bimatoprost and PLGA, evaporating the liquid from the emulsion to form an evaporated product, suspending and rinsing the evaporated product, and drying the evaporated product.

In accordance with the disclosure herein, an embodiment of the present invention is a population of microparticles that comprise a polymeric component encapsulating a prostamide component in the form of oil-in-oil emulsified microparticles. In one specific embodiment, the polymeric component comprises a PLGA copolymer and the prostamide component comprises at least one prostamide derivative selected from the group consisting of bimatoprost, salts thereof, and mixtures thereof.

The resulting population may be a terminally sterilized population of microparticles. Terminally sterilized microparticles retain their therapeutic activity during storage and therefore can provide successful treatment to patients. In certain embodiments, a major portion of the prostamide component of the terminally sterilized microparticles remains stable. For example, in certain embodiments, at least 80% of the prostamide component remains stable after sterilization. In further embodiments, at least 90%, at least 95%, or at least 99% of the prostamide component remains stable.

In addition, the present population of microparticles may have a maximum particle diameter less than about 200 μm. In certain embodiments, the population of microparticles has an average or mean particle diameter less than about 50 μm. In further embodiments, the population of microparticles has a mean particle diameter from about 30 μm to about 50 μm.

The present microparticles are structured or configured to release the prostamide component for extended periods of time at controlled rates. In some embodiments, the prostamide component is released at a substantially linear rate (e.g., a single rate) over the life of the microparticles (e.g., until the microparticles fully degrade). Other embodiments are capable of releasing the prostamide component at multiple rates or different rates over the life of the microparticles. The rate at which the microparticles degrade can vary, as discussed herein, and therefore, the present microparticles can release the prostamide component for different periods of time depending on the particular configuration and materials of the microparticles. In at least one embodiment, a microparticle can release about 1% of the prostamide component in the microparticles per day. In a further embodiment, the microparticles may have a release rate of about 0.7% per day when measured in vitro. Thus, over a period of about 40 days, about 30% of the prostamide component may have been released.

As discussed herein, the amount of the prostamide component present in the microparticles can vary. In certain embodiments, the about 10% wt/wt of the microparticles is the prostamide component. In further embodiments, the prostamide component constitutes about 5% wt/wt of the microparticles.

The implants, including the population of microparticles, of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate). In addition, the present implants, including microparticles, can be administered to other ocular regions outside of the vitreous. Microparticles may be administered to patients by administering an ophthalmically acceptable composition which comprises the microparticles to the patient. For example, microparticles may be provided in a liquid composition, a suspension, an emulsion, and the like, and administered topically or by injection or implantation into one or more non-vitreal regions of the eye.

The present implants or microparticles are configured to release an amount of prostamide component effective to treat an ocular condition, such as by reducing at least one symptom of the ocular condition. More specifically, the implants or microparticles may be used in a method to treat glaucoma, such as open angle glaucoma, ocular hypertension, chronic angle-closure glaucoma, with patent iridotomy, psuedoexfoliative glaucoma, and pigmentary glaucoma. By implanting the prostamide component-containing implants into the vitreous of an eye, it is believed that the prostamide component is effective to enhance aqueous humour flow thereby reducing intraocular pressure. In addition, placement of the microparticles described herein outside of the vitreous can also provide similar therapy.

The implants disclosed herein may also be configured to release the prostamide component or additional therapeutic agents, as described above, which to prevent or treat diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Sceritis, Serpignous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch Angitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveltic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Systemic Disorders with Associated Retinal Dystrophies, Congenital Stationary Night Blindness, Cone Dystrophies, Fundus Flavimaculatus, Bests Disease, Pattern Dystrophy of the Retinal Pigmented Epithelium, X-Linked Retinoschisis, Sorsby's Fundus Dystrophy, Benign Concentric Maculopethy, Biett's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjuctval injection, sub-tenon injections, retrobulbar injection, and suprachoroidal injection.

In at least one embodiment, a method of reducing intraocular pressure in an eye of a patient comprises administering one or more implants containing a prostamide component, as disclosed herein to a patient by at least one of intravitreal injection, subconjuctval injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the prostamide component from the implants.

In addition, for dual therapy approaches to treating an ocular condition, the method may include one or more additional steps of administering additional therapeutic agents to the eye, such as by topically administering compositions containing timolol, dorzalamide, and iatoprost, among others.

In another aspect of the invention, kits and packages for treating an ocular condition of the eye are provided, comprising: a) a container comprising an extended release implant comprising a therapeutic component including a prostamide component, such as bimatoprost (Lumigan), and a drug release sustaining component; and b) instructions for use. Instructions may include steps of how to handle the implants, how to insert the implants into an ocular region, and what to expect from using the implants.

In certain implants, the implant comprises a therapeutic component which consists essentially of bimatoprost, salts thereof, and mixtures thereof, and a biodegradable polymer matrix. The biodegradable polymer matrix may consist essentially of PLA, PLGA, or a combination thereof. When placed in the eye, the implant releases about 40% to about 60% of the bimatoprost to provide a loading dose of the bimatoprost within about one day after placement in the eye. Subsequently, the implant releases about 1% to about 2% of the bimatoprost per day to provide a sustained therapeutic effect. Such implants may be effective in reducing and maintaining a reduced intraocular pressure, such as below about 15 mm Hg for several months, and potentially for one or two years.

Other implants disclosed herein may be configured such that the amount of the prostamide component that is released from the implant within two days of being placed in the eye is less than about 95% of the total amount of the prostamide component in the implant. In certain implants, 95% of the prostamide component is not released until after about one week of being placed in an eye. In certain implants, about 50% of the prostamide component is released within about one day of placement in the eye, and about 2% is released for about 1 month after being placed in the eye. In other implants, about 50% of the prostamide component is released within about one day of placement in the eye, and about 1% is released for about 2 months after being placed in the eye.

EXAMPLES

Example 1

Manufacture and Testing of Implants Containing Bimatoprost and a Biodegradable Polymer Matrix Biodegradable implants were made by combining bimatoprost with a biodegradable polymer composition. 800 mg of polylactic acid (PLA) was combined with 200 mg of bimatoprost. The combination was dissolved in 25 milliliters of dichloromethane. The mixture was placed in a vacuum at 45° C. overnight to evaporate the dichloromethane. The resulting mixture was in the form of a cast sheet. The cast sheet was cut and ground in a high shear grinder with dry ice until the particles could pass through a sieve having a pore size of about 125 μm. The percent of bimatoprost present in the microparticles was analyzed using high pressure liquid chromatography (HPLC). The percent release of bimatoprost from the microparticles was profiled using dialysis. The percent of bimatoprost remaining in the recovered particles was analyzed by HPLC.

The release profile is described in Table 1.

| Time Point | Elapsed Time (Days) | Percent Released | Percent Per Day |
|---|---|---|---|
| Start | 0 | — | — |
| 1 | 1.03 | 47.51 | 47.51 |
| 2 | 2.03 | 47.92 | 0.41 |
| 3 | 3.03 | 49.99 | 2.07 |
| 4 | 4.03 | 50.09 | 0.10 |
| 5 | 7.04 | 50.90 | 0.82 |

The percent loading of bimatoprost was 14.93%. The percent of bimatoprost remaining in the recovered release particles was 4.94%.

Example 2

Extrusion Process and Compression of Manufacturing Bimatoprost-Containing Biodegradable Intraocular Implants Bimatoprost is combined with a biodegradable polymer composition in a mortar. The combination is mixed with a shaker set at about 96 RPM for about 15 minutes. The powder blend is scraped off the wall of the mortar and is then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods may have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing is performed by placing each implant into a 24 mL screw cap vial with 10 mL of Phosphate Buffered Saline solution at 37° C. 1 mL aliquots are removed and are replaced with equal volume of fresh medium on day 1, 4, 7, 14, 28, and every two weeks thereafter.

Drug assays are performed by HPLC, which consists of a Waters 2690 Separation Module (or 2696), and a Waters 2996 Photodiode Array Detector. An Ultrasphere, C-18 (2), 5 μm; 4.6×150 mm column heated at 30° C. is used for separation and the detector is set at about 264 nm. The mobile phase is (10:90) MeOH-buffered mobile phase with a flow rate of 1 mL/min and a total run time of 12 min per sample. The buffered mobile phase may comprise (68:0.75:0.25:31) 13 mM 1-Heptane Sulfonic Acid, sodium salt-glacial acetic acid-triethylamine-Methanol. The release rates are determined by calculating the amount of drug being released in a given volume of medium over time in μg/day.

Polymers which may be used in the implants can be obtained from Boehringer Ingelheim. Examples of polymer include: RG502, RG752, R202H, R203 and R206, and Purac PDLG (50/50), RG502 is (50:50) poly(D,L-lactide-co-glycolide), RG752 is (75:25) poly(D,L-lactide-co-glycolide), R202H is 100% poly(D,L-lactide) with acid end group or terminal acid groups, R203 and R206 are both 100% poly(D.L-lactide). Purac PDLG (50150) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 3

Bimatoprost/PLA/PLGA Intraocular Implants to Treat Glaucoma

A 72 year old female suffering from glaucoma in both eyes receives an intraocular implant containing bimatoprost and a combination of a PLA and PLGA in each eye. The implants weigh about 1 mg, and contain about 500 mg of bimatoprost. One implant is placed in the vitreous of each eye using a syringe. In about two days, the patient reports a substantial relief in ocular comfort. Examination reveals that the intraocular pressure has decreased, the average intraocular pressure measured at 8:00 AM has decreased from 28 mm Hg to 14.3 mm Hg. The patient is monitored monthly for about 6 months. Intraocular pressure levels remain below 15 mm Hg for six months, and the patient reports reduced ocular discomfort.

Example 4

Bimatoprost/PLA Intraocular Implants to Reduce Ocular Hypertension

A 62 year old male presents with an intraocular pressure in his left eye of 33 mm Hg. An implant containing 400 mg of bimatoprost and 600 mg of PLA is inserted into the vitreous of the left eye using a trocar. The patient's intraocular pressure is monitored daily for one week, and then monthly thereafter. One day after implantation, the intraocular pressure is reduced to 18 mm Hg. By day 7 after implantation, the intraocular pressure is relatively stable at 14 mm Hg. The patient does not experience any further signs of elevated intraocular pressure for 2 years.

Example 5

Microencapsulation of a Prostamide Derivative

This example describes a process for producing microparticles that include a prostamide derivative encapsulated by a biodegradable polymer. In the specific example, bimatoprost was used as the prostamide derivative. The procedures outlined herein can be used to make encapsulated microparticles of other prostamide derivatives as well.

FIG. 1 is a flow chart illustrating the steps used in the method of this example.

As shown in FIG. 1, a first composition was formed by adding 100 mg of bimatoprost to 20 mL of acetonitrile ($CH_3CN$) in an Erlenmeyer flask with a magnetic stirrer and stopper. The bimatoprost was solubilized in the acetonitrile. PLGA (900 mg) was added to the solubilized composition and stirred until the PLGA was solubilized. This first composition can be understood to be a discontinuous phase or an acetonitrile phase composition.

A second composition was formed by combining 800 mL of cottonseed oil and 12.8 mL of Span® 85 in a 1000 mL beaker. Span® 85 is a fatty acid composition which comprises oleic acid (C18:1) approx. 74%; linoleic acid (C18:2) approx. 7%; linolenic acid (C18:2) approx. 2%; palmitoleic acid (C16:1) approx. 7%; and palmitic add (C16:0). Span is a registered trademark of ICI Americas, Inc., and the Span® 85 can be obtained from public sources, such as Sigma Aldrich. Other Span® products can also be used, such as Span® 80. This composition can be understood to be a continuous phase or oil-containing composition.

An emulsion was formed by adding the first composition to the second composition. The speed impeller was set at 350 rotations per minute (rpm) to stir the second composition. The first composition was added to the stirring second composition, and the mixture was allowed to stir for 90 minutes.

The emulsion was then evaporated under filter air flow for 45 hours at 250 rpm air flow.

Hexane (250 mL) was added to the evaporated product and stirred for 1 hour. Subsequently, the suspension was centrifuged at 7000 rpm for 10 minutes.

The pellet containing microparticles was rinsed twice by centrifuging with 100 mL of hexane. The microparticles were resuspended in 15 mL of hexane.

The microspheres were then dried under filter air flow overnight.

Microspheres were packaged under nitrogen and reduced temperatures to maintain the temperature at about 5 C. The cooled microspheres were sterilized using gamma radiation (25-35 kGy).

Figure 2A:
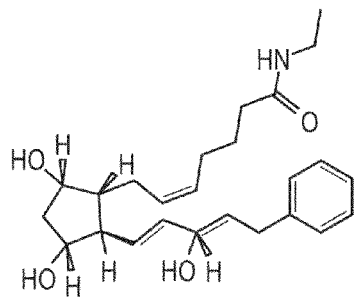
FIG. 2A is the chemical structure of bimatoprost.
Figure 2B:
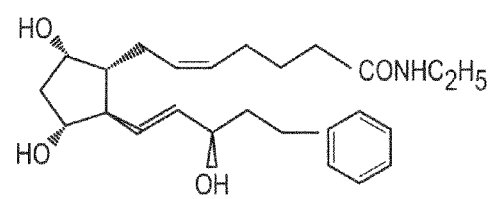
FIG. 2B is the chemical structure of 15β bimatoprost.
Figure 2C:
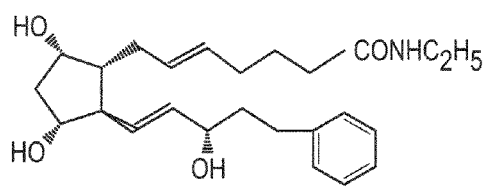
FIG. 2C is the chemical structure of 5,6,-trans bimatoprost isomer.
Figure 2D:
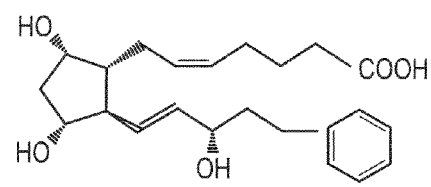
FIG. 2D is the chemical structure of the C1 acid of bimatoprost.
Figure 2E:
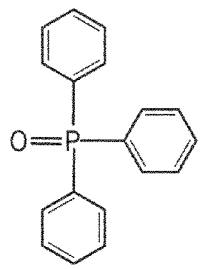
FIG. 2E is the chemical structure of triphenylphosphine oxide.
Figure 2F:
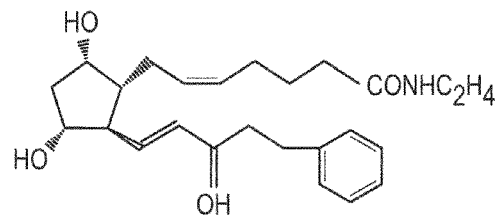
FIG. 2F is the chemical structure of 15-Keto bimatoprost.

FIGS. 2A, 2B, 2C, 2D, 2E, and 2F illustrate the chemical structure of bimatoprost (AGN 192024, FIG. 2A), 15β bimatoprost (FIG. 2B); 5,6-trans bimatoprost isomer (FIG. 2C): C1 add of bimatoprost (FIG. 2D); triphenyphosphine oxide (TPPO; FIG. 2E); and 15-Keto bimatoprost (FIG. 2F). Bimatoprost is the active ingredient and the other chemicals are impurities that may be present. Bimatoprost has a molecular weight of 415.6 g/mol, a solubility in water at room temperature of 3.2 mg/mL (which is slightly soluble), and a partition coefficient Log P of 2.4 plus or minus 0.1. Bimatoprost is a non-ionisable compound.

The effects of gamma sterilization on the stability of bimatoprost are presented in the following table (Table 2). The formula abbreviations correspond to compounds illustrated in FIGS. 2A-2F.

| Bimatoprost | % wt/wt bimatoprost | % wt/wt. 15-keto | % wt/wt 15β | % wt/wt 5,6-trans |
| --- | --- | --- | --- | --- |
| none sterilized | 95.3 | 1.0 | 0.2 | 0.1 |
| gamma sterilized | 85.3 | 2.3 | 0.1 | 0.1 |

Gamma sterilization appeared to decrease the amount of active bimatoprost by about 10%. Gamma sterilization may also change the color of the material (e.g., from white to a yellow/brown) and the consistency of the material (e.g., from a fluffy powder to a more compact powder).

Two separate batches of microparticles were produced using PLGA copolymers from different suppliers, as presented in Table 3, below

| Supplier | Batch Number | Lactide/Glycolide ratio Random/Block End-groups | Molecular Weight | Inherent Viscosity |
| --- | --- | --- | --- | --- |
| APT | 1 | 75/25 Random Ester & Hydroxyl | 63,200 Da | 0.65 dL/g |
| BPI | 2 | 75/25 Random Ester & Hydroxyl | ~97,100 Da | 0.67 dL/g |

APT in Table 3 refers to Absorbable Polymer Technologies, and BPI refers to Birmingham Polymers, Inc. The PLGA obtained from APT appeared to provide better results than PLGA from BPI.

Figure 3A:
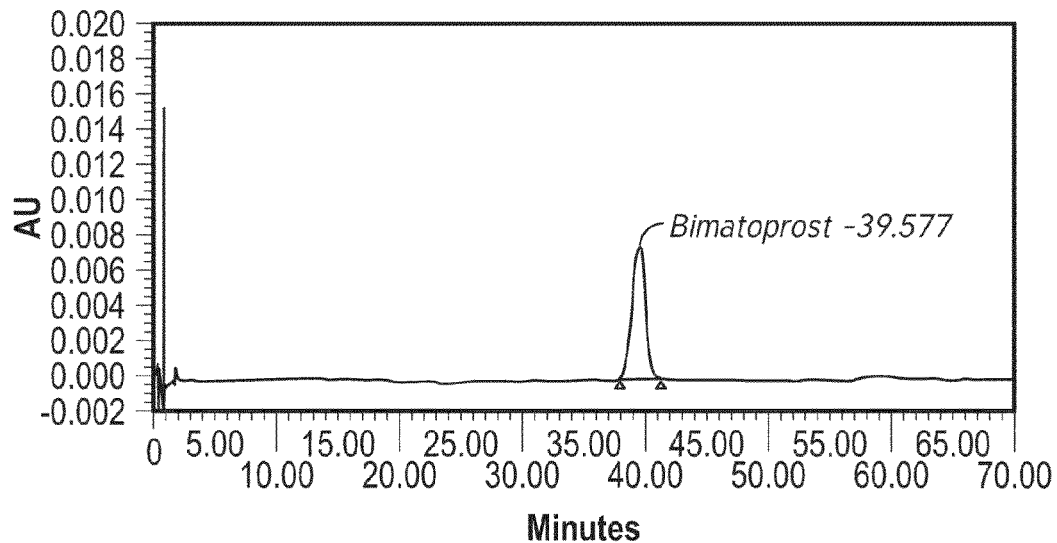
FIG. 3A is a chromatogram of a bimatoprost standard.
Figure 3B:
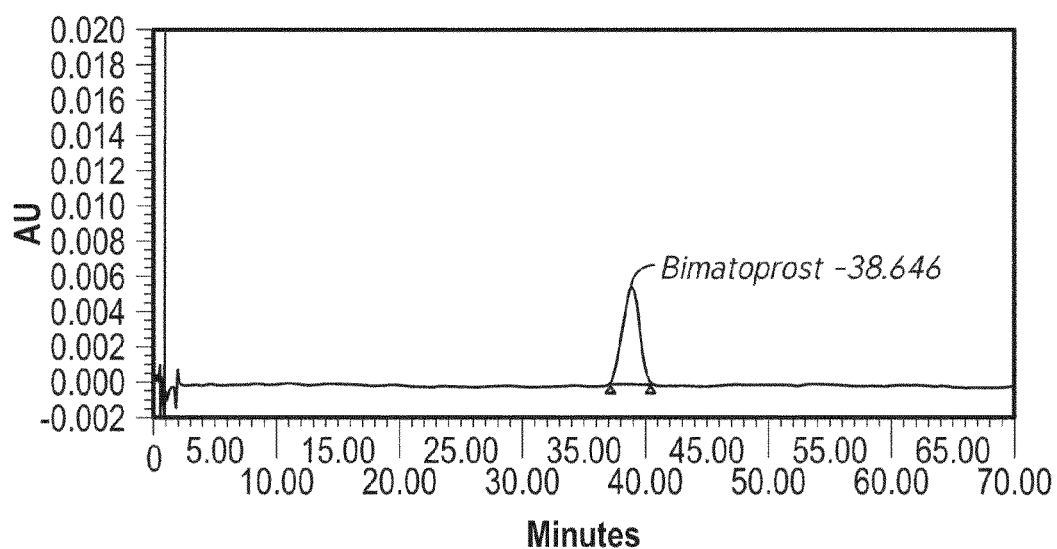
FIG. 3C is a chromatogram of sterilized bimatoprost microparticles.
FIG. 3D is a chromatogram of non-sterilized placebo compositions.
FIG. 3E is a chromatogram of sterilized placebo compositions.
Figure 3C:
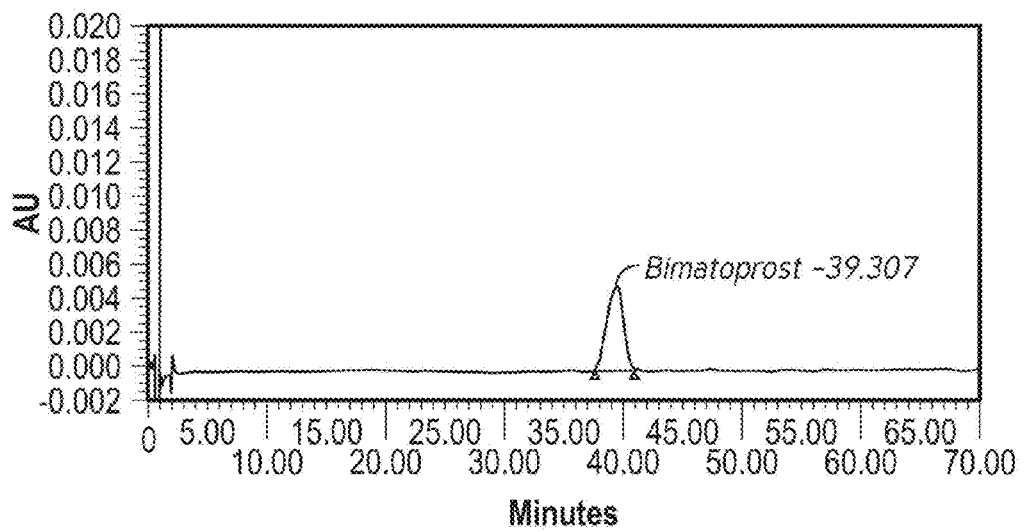
Figure 3D:
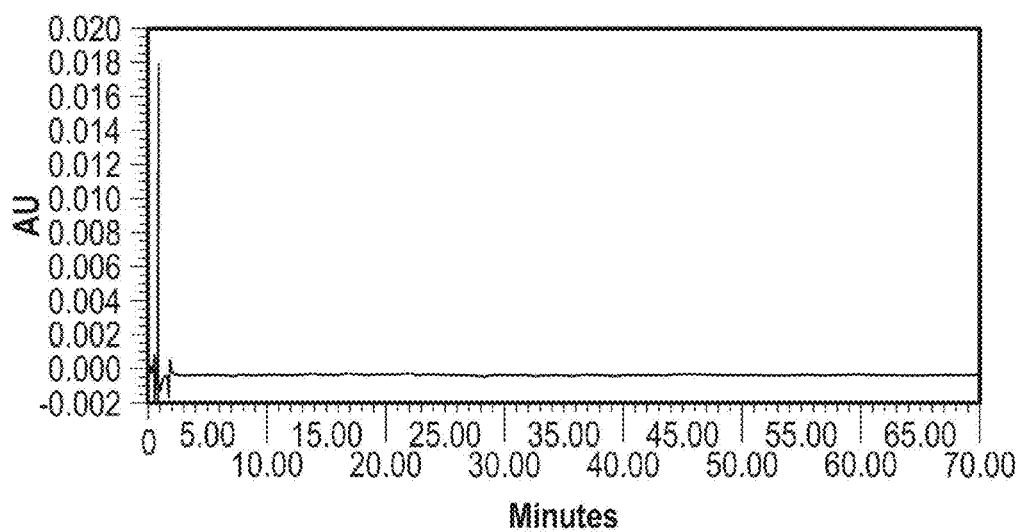
Figure 3E:
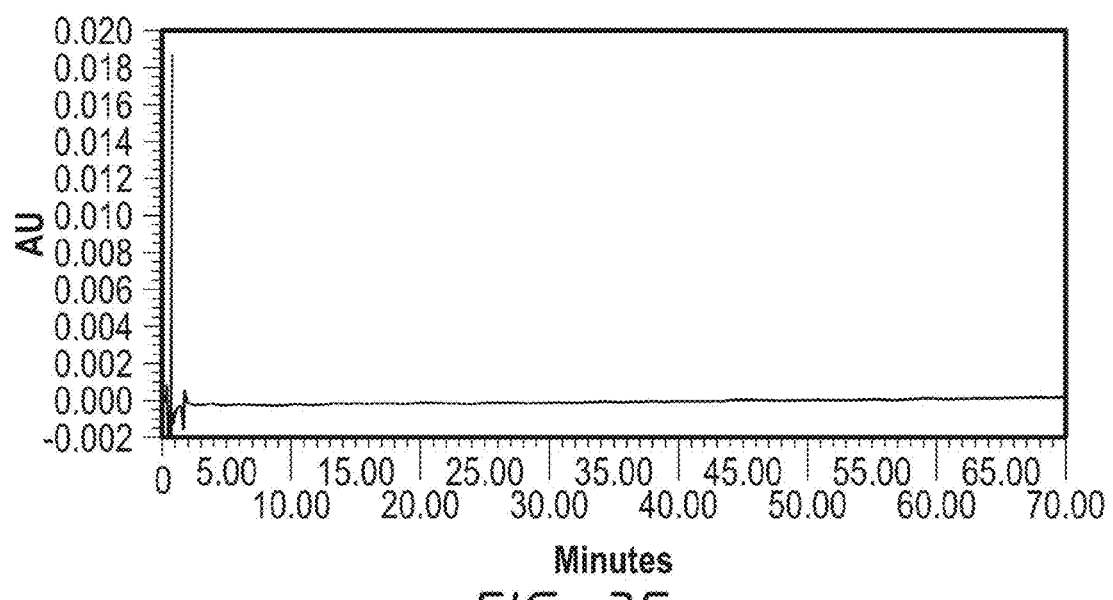

High performance liquid chromatography was used to quantify bimatoprost and impurities present in the microparticles. Analytes were eluted from a Waters Symmetry® C18 reverse-phase column using a mobile phase composed of 72/18/10 (water/acetonitrile/methanol v/v/v) containing 0.03% (w/v) trifluoroacetic acid. UV detection was performed at 210 nm. Chromatograms of a bimatoprost standard (FIG. 3A), a non-sterilized and sterilized placebo compositions (FIG. 3D and FIG. 3E), and non-sterilized and sterilized bimatoprost microparticles (FIG. 3B and FIG. 3C) revealed that the microparticles did not contain detectable amounts of impurities as evidenced by the single absorption peak in FIGS. 3A-C.

Figure 4A:
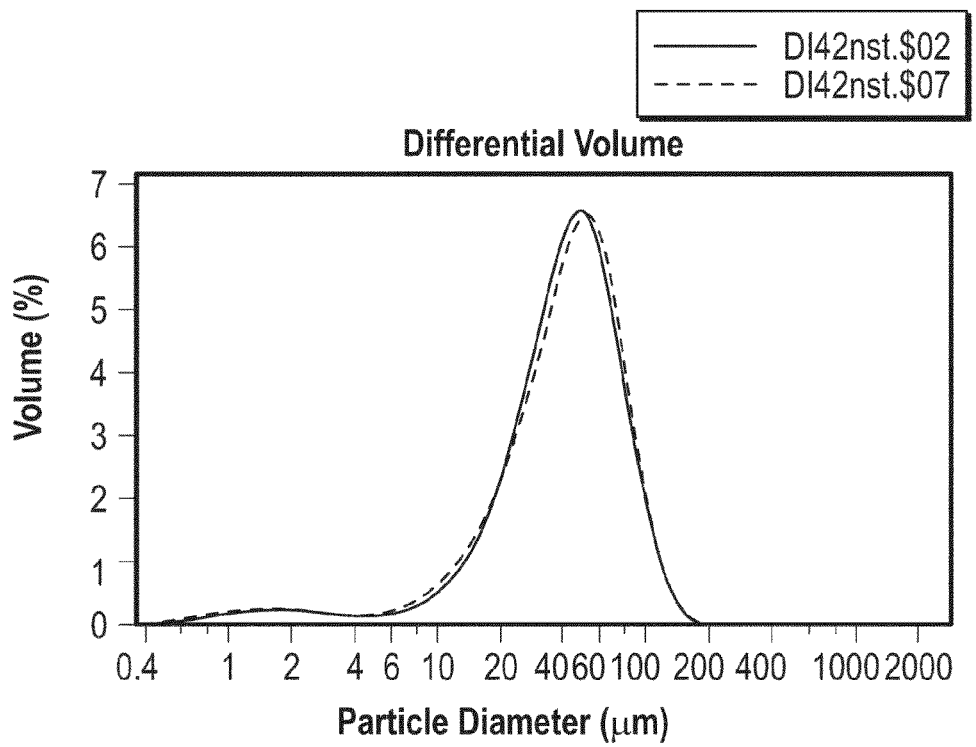
FIG. 4A is a graph of volume % as a function of particle diameter.
Figure 4B:
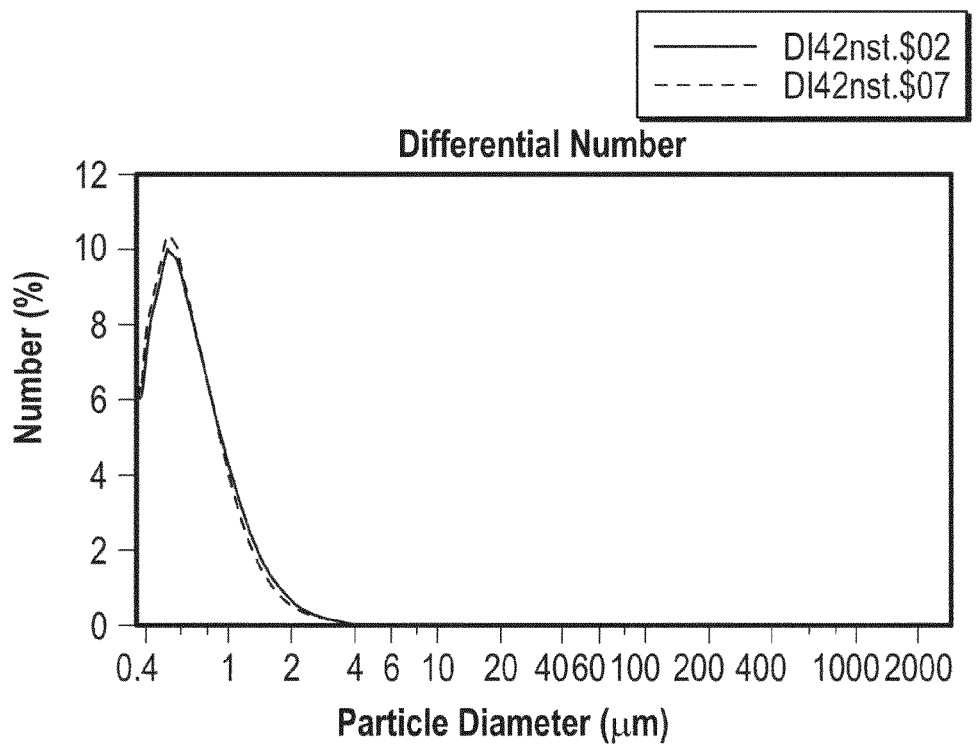
FIG. 4B is a graph of number % as a function of particle diameter.
Figure 4C:
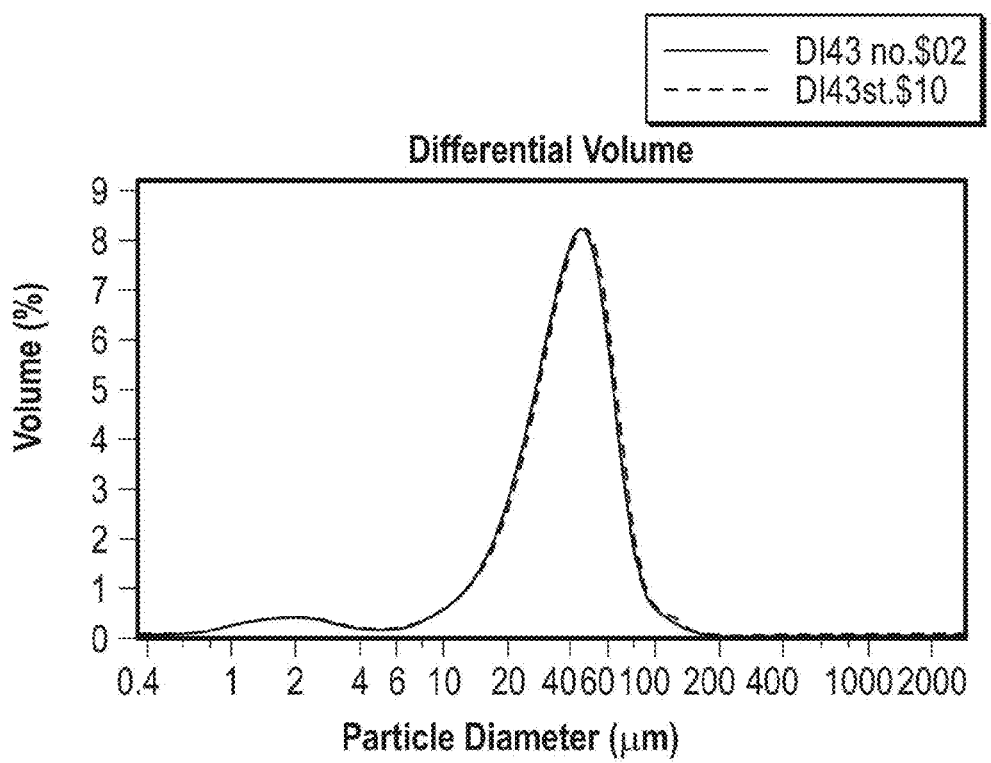
FIG. 4C is a graph of volume % as a function of particle diameter for a different batch of microparticles than shown in FIG. 4A.
Figure 4D:
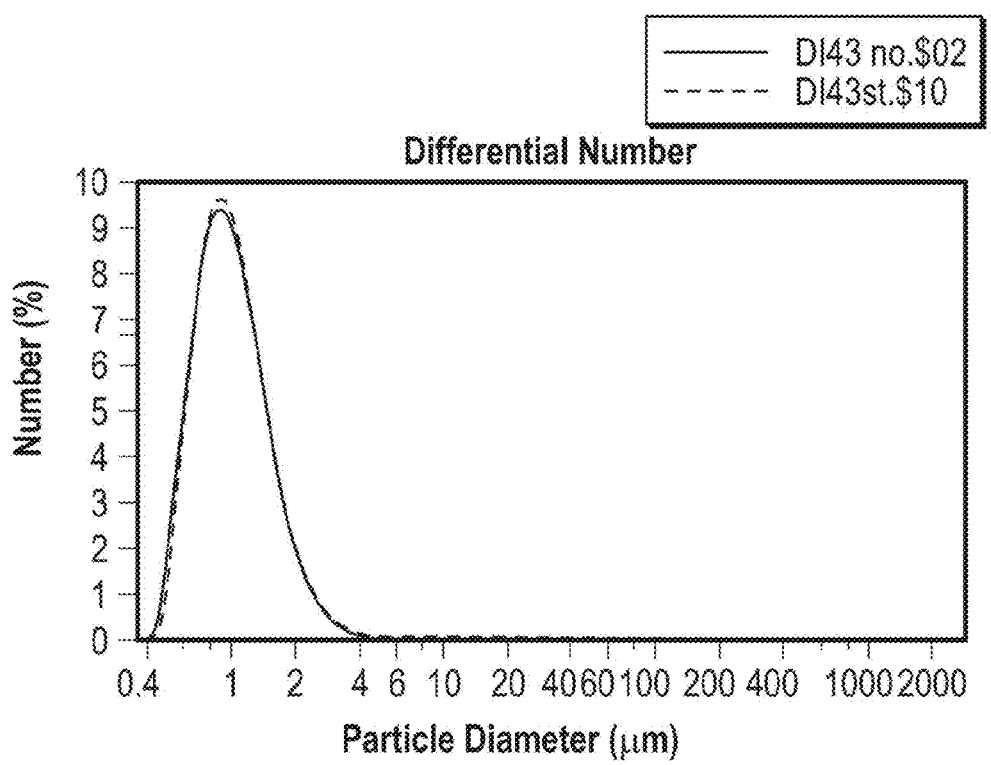
FIG. 4D is a graph of number % as a function of particle diameter for the batch of FIG. 4C.

Particle size was determined by suspending an aliquot of the bimatoprost microspheres in 1 mL of deionized water. To this, 100 μL of 10% Tween 80 was added. The composition was sonicated for 5 minutes and vortexed for 15 seconds. A Coulter LS230 apparatus or equivalent apparatus were used to measure particle size. Mean particle diameters of tested batches were between about 30 μm and about 50 μm. Some particles had diameters up to about 200 μm. These larger particles were observed in batches that were not sieved. FIGS. 4A-4D illustrate particle diameters (differential volume and number) profile superposition for sterile and non sterile conditions. Each graph illustrates the particle diameter distribution for a batch of sterile microspheres and non-sterile microspheres. The data reveal that sterilization did not significantly impact the particle size distribution as evidenced by the substantial overlap in the distribution curves. FIG. 4A illustrates volume % as a function of particle diameter for batch DL042 (top left panel), FIG. 4B illustrates number % as a function of particle diameter for batch DL042 (top right panel), FIG. 4C illustrates volume % as a function of particle diameter for batch DL043 (bottom left panel), and FIG. 4D illustrates number % as a function of particle diameter for batch DL043 (bottom right panel).

Figure 5A:
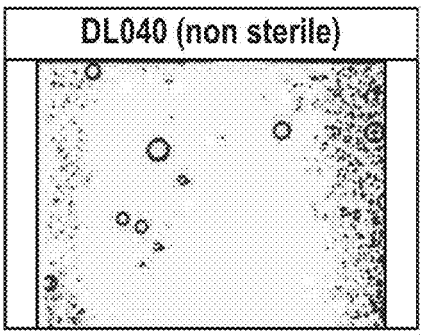
FIG. 5A is a photograph of one batch of sterile microspheres.
Figure 5B:
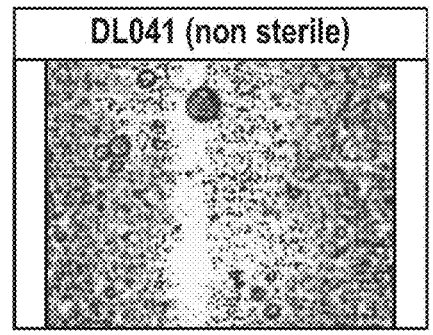
FIG. 5B is a photograph of a different batch of sterile microspheres other than the batch of FIG. 5A.
Figure 5C:
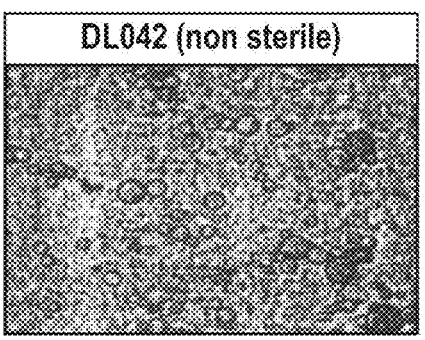
FIG. 5C is a photograph of of non-sterile microspheres.
Figure 5D:
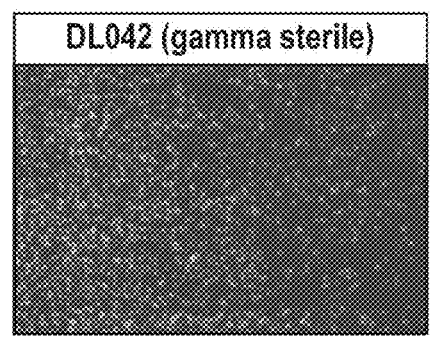
FIG. 5D is a photograph of sterile microspheres.
Figure 5E:
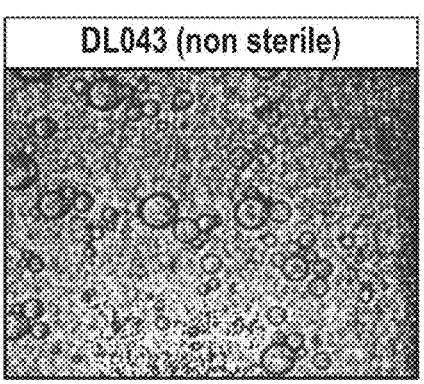
FIG. 5E is a photograph of a non-sterile batch of microspheres.
Figure 5F:
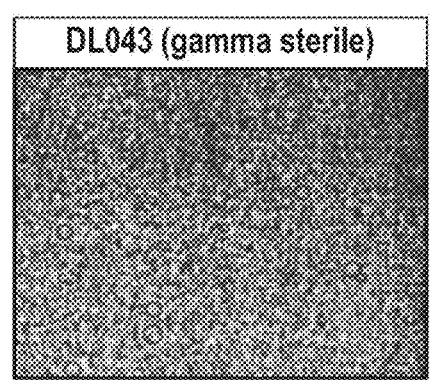
FIG. 5F is a photograph of sterile microspheres.

Microscopic aspect was determined using the sample prepared for particle size determination, described above. Observations were performed at magnification 5 and 20. FIGS. 5A-5F illustrate shapes of four different non-sterile and two different sterile batches of microspheres (FIG. 5A and FIG. 5B (top two panels) and FIGS. 5C and 5E illustrate non-sterile batches and FIG. 5D and FIG. 5F (bottom two right panels) illustrate sterile batches of microspheres).

Figure 6:
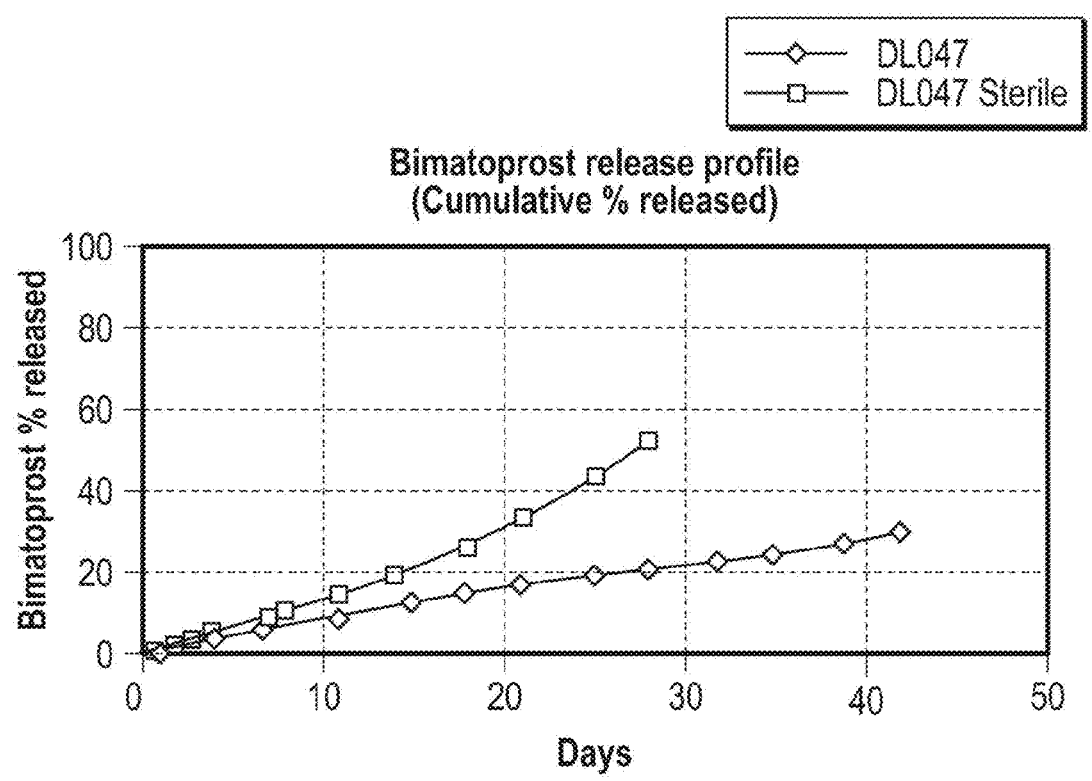
FIG. 6 is a graph percent bimatoprost released as a function of time.

The dissolution profile for a batch of microparticles was monitored for 28 and 42 days for sterile and non-sterile microspheres using dialysis bags and dissolution media. The dissolution media was phosphate buffer (pH 7.4) and ethanol in a ratio of 90/10. Samples were monitored at 37 C. in a shaker water bath at approximately 110 rpm. At each time point, an aliquot of sample was collected and replaced by fresh media. The dissolution profile for a batch of sterile and non-sterile microspheres is shown in FIG. 6. The dissolution rate for the non-sterile microparticles was about 0.7%/day (e.g., 30% released over 42 days). The dissolution rate for the sterile batch initially appeared to be about 0.7%/day and increased after about two weeks. FIG. 6 also shows that bimatoprost was released faster from gamma sterilized microspheres than non-sterilized microspheres.

Table 4 below provides information regarding the batches of microspheres prepared in accordance with the present methods and as discussed above.

| Batch No. | PLGA type/SPAN type | Sterilized (Yes/No) |
| --- | --- | --- |
| DL040 | PLGA APT 75/25/ iv 0.65/SPAN 80 | No |
| DL041 | APT/SPAN 85 | No |
| DL042 | APT/SPAN 80 | No |
| DL042 | APT/SPAN 80 | Yes |
| DL043 | APT/SPAN 80 | No |
| DL043 | APT/SPAN 80 | Yes |

In Table 4, APT refers to the PLGA supplier, as discussed herein, iv refers to inherent viscosity, and SPAN refers to the fatty acid composition described herein, and which is publicly available.

Table 5 below provides information regarding the amount of bimatoprost present in non-sterile microspheres. In these microspheres, bimatoprost was present in an amount of about 5% w/w.

| Batch No. | Targeted loading | % w/w bimatoprost |
| --- | --- | --- |
| DL040 | 10% | 4.6 |
| DL041 | 10% | 5.1 |
| DL042 | 10% | 4.8 |
| DL043 | Placebo | ND |

Batches DL042 and DL043 were gamma sterilized (25-35 kGy) in order to evaluate the stability of the active ingredient when encapsulated within PLGA. The results are presented in Table 6 below.

| Batch No. | Targeted Loading | % w/w bimatoprost | % w/w keto |
| --- | --- | --- | --- |
| DL042 | 10% | 4.3 | ND |
| DL042 sterile | 10% | 4.2 | ND |
| DL043 | Placebo | ND | ND |
| DL043 sterile | Placebo | ND | ND |

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

What is claimed is:

1. A method for producing therapeutic polymeric microparticles, comprising: encapsulating a prostamide component with a polymeric component to form a population of prostamide-encapsulated microparticles by an oil-in-oil emulsion process, wherein the prostamide component comprises a combination of two or more different prostamide derivatives.

2. The method of claim 1, wherein the oil-in-oil emulsion process comprises forming an oil-in-oil emulsion containing the prostamide component and the polymeric component; drying the emulsion to form a dried emulsion product; contacting the dried emulsion product with a solvent to form a solvent-containing composition; and removing the solvent from the solvent-containing composition to form the population of microparticles comprising the prostamide component and the polymeric component.

3. The method of claim 1, wherein the prostamide component of the microparticles so produced is encapsulated by the polymeric component to preserve therapeutic activity of the prostamide component after a terminal sterilization procedure.

4. The method of claim 1, wherein the polymeric component comprises a biodegradable polymer or biodegradable copolymer.

5. The method of claim 1, wherein the polymeric component comprises a poly(lactide-co-glycolide) PLGA copolymer.

6. The method of claim 5, wherein the PLGA copolymer has a lactide/glycolide ratio of 75/25 a molecular weight of about 63 kilodaltons, and an inherent viscosity of about 0.6 dL/g.

7. The method of claim 2, further comprising forming a first composition comprising the prostamide component, the polymeric component, and an organic solvent, and forming a second oil-containing composition, wherein the forming the oil-in-oil emulsion step comprises mixing the first composition and the second oil containing composition.

8. The method of claim 2, wherein the drying comprises evaporating the oil-in-oil emulsion to form an evaporated product.

9. The method of claim 8, further comprising suspending the evaporated product in the solvent before removing the solvent from the solvent-containing composition.

10. The method of claim 1, further comprising terminally sterilizing the polymeric microparticles.

11. The method of claim 1, wherein the prostamide component comprises bimatoprost and latanoprost.

12. The method of claim 1, wherein the prostamide component comprises bimatoprost and travoprost.

* * * * *